(12) United States Patent
Xu et al.

(10) Patent No.: US 8,081,807 B2
(45) Date of Patent: Dec. 20, 2011

(54) METHOD AND DEVICE OF RECONSTRUCTING AN (N+1)-DIMENSIONAL IMAGE FUNCTION FROM RADON DATA

(75) Inventors: Yuan Xu, Eugene, OR (US); Oleg Tischenko, München (DE); Christoph Hoeschen, Hebertshausen (DE)

(73) Assignees: State of Oregon Acting by and through the State Board of Higher Education on Behalf of the University of Oregon, Eugene, OR (US); Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 1008 days.

(21) Appl. No.: 11/794,558

(22) PCT Filed: Dec. 21, 2005

(86) PCT No.: PCT/EP2005/013801
§ 371 (c)(1), (2), (4) Date: Jan. 17, 2008

(87) PCT Pub. No.: WO2006/069708
PCT Pub. Date: Jul. 6, 2006

(65) Prior Publication Data
US 2008/0130974 A1 Jun. 5, 2008

Related U.S. Application Data

(60) Provisional application No. 60/640,426, filed on Dec. 30, 2004.

(30) Foreign Application Priority Data

Dec. 30, 2004 (EP) ..................................... 04031043

(51) Int. Cl.
*G06K 9/00* (2006.01)
*A61B 6/00* (2006.01)
(52) U.S. Cl. ........................... 382/128; 382/280; 378/19
(58) Field of Classification Search .................. 382/100, 382/128, 129, 130, 131, 132, 133, 134, 154, 382/168, 173, 181, 184, 194, 232, 254, 274, 382/276, 285–289, 295, 305, 312, 280; 378/10, 378/19, 21, 4, 15
See application file for complete search history.

(56) References Cited

U.S. PATENT DOCUMENTS

| | | | | |
|---|---|---|---|---|
| 4,315,157 A | * | 2/1982 | Barnes ............................ | 378/10 |
| 5,592,523 A | * | 1/1997 | Tuy et al. ........................ | 378/19 |
| 6,343,110 B1 | * | 1/2002 | Li .................................. | 378/19 |

(Continued)

OTHER PUBLICATIONS

Kalender, "Computed Tomography—Fundamentals, System Technology, Image Quality, Applications," Chapter 2, (2000).

(Continued)

*Primary Examiner* — Seyed Azarian
(74) *Attorney, Agent, or Firm* — Klarquist Sparkman, LLP

(57) ABSTRACT

A method of reconstructing an (n+1)-dimensional image function $f$ representing a region of investigation comprises determining the image function $f$ from n-dimensional or less dimensional Radon data comprising a plurality of projection functions $p_\Theta(t)$ measured corresponding to a plurality of predetermined projection directions ($\Theta$), wherein the image function $f$ is determined as a sum of polynomials multiplied with values of the projection functions $p_\Theta(t)$. Imaging methods, imaging devices, and computer tomography devices using this reconstruction method are described.

53 Claims, 8 Drawing Sheets

U.S. PATENT DOCUMENTS

| | | | |
|---|---|---|---|
| 6,944,259 B2* | 9/2005 | Yang | 378/15 |
| 2009/0245456 A1* | 10/2009 | Tischenko et al. | 378/4 |
| 2009/0297009 A1* | 12/2009 | Xu et al. | 382/131 |

OTHER PUBLICATIONS

Herman "Image Reconstruction from Projections: The Fundamentals of Computerized Tomography," Academic Press, Chapter 6, (1980).

R. Marr, "On the Reconstruction of a Function on a Circular Domain from a Sampling of its Line Integrals," J. Math. Anal. Appl., 45:357-374, (1974).

F. Natterer: "The Mathematics of Computerized Tomography," Reprint of the 1986 original Classics in Applied Mathematics 32 SIAM, Philadelphia, PA, (2001).

F. Natterer and F. Wuebbeling "Mathematical Methods in Image Reconstruction," SIAM, Philadelphia, PA, (2001).

C. Dunkl and Yuan Xu "Orthogonal Polynomials of Several Variables," Cambridge University Press, Chapter 6, (2001).

Yuan Xu "Funk-Hecke Formula for Orthogonal Polynomials on Spheres and on Balls," in Bull. London Math. Soc., 32:447-457, (2000).

Yuan Xu "Representation of Reproducing Kernels and the Lebesgue Constants on the Ball" in J. Approximation Theory, 112:295-310, (2001).

International Search Report and Written Opinion from related application PCT/EP2005/013801, Mar. 3, 2006.

International Preliminary Examination Report from related application PCT/EP2005/013801, Dec. 22, 2006.

Bortfeld T. et al., "Fast and exact 2D image reconstruction by means of Chebyshev decomposition and backprojection," Physics in Medicine and Biology 44:1105-1120 (Apr. 1999).

Hanson and Wecksung, "Local basis-function approach to computed tomography," Appl. Opt. 24:4028-4039 (Dec. 1985).

* cited by examiner

METHOD AND DEVICE OF RECONSTRUCTING AN (N+1)-DIMENSIONAL IMAGE FUNCTION FROM RADON DATA

CROSS-REFERENCE TO RELATED APPLICATIONS

This is the U.S. National Stage of International Application No. PCT/EP2005/013801, filed Dec. 21, 2005, which was published in English under PCT Article 21(2), which in turn claims the benefit of U.S. Provisional Application No. 60/640,426, filed Dec. 30, 2004, and European Patent Application No. 04031043.5, filed Dec. 30, 2004. These applications are incorporated herein by reference.

ACKNOWLEDGEMENT OF GOVERNMENT SUPPORT

This invention was made with Government support under Grant No. DMS-02011669 awarded by the National Science Foundation, U.S.A. The Government of the United States of America has certain rights in the invention.

TECHNICAL FIELD

The present invention relates to a method of reconstructing an (n+1)-dimensional image function from n-dimensional or less dimensional Radon data comprising a plurality of projection functions measured corresponding to a plurality of predetermined projection directions. Furthermore, the present invention relates to a method and a device for imaging a region of investigation on the basis of the above reconstructing method.

TECHNICAL BACKGROUND

The non-destructive investigation of samples is an important object in various technical fields like material sciences, medical examinations, archaeology, construction technique, techniques concerning security matters etc. One approach for obtaining an image of a sample e.g. by computer tomography (CT) is based on an irradiation trough a sample plane from different projection directions with X-rays, followed by the reconstruction of the sample plane on the basis of attenuation data measured at different directions. The entirety of the measured attenuation data can be described in terms of so-called Radon data in a Radon space.

Different reconstruction methods for Radon data are known today. For an introduction to the mathematical and physical principles of conventional image reconstruction, reference is made to the textbooks "Computed Tomography—Fundamentals, System Technology, Image Quality, Applications" by W. A. Kalender (1$^{st}$. edition, ISBN 3-89578-081-2); "Image Reconstruction from Projections: The Fundamentals of Computerized Tomography" by G. T. Herman, Academic Press, 1980; and "Einführung in die Computertomographie" by Thorsten M. Buzug (Springer-Verlag, Berlin 2004). The conventional reconstruction methods can be summarized as methods based on the iterative reconstruction or those based on the so-called filtered back-projection.

The iterative reconstruction is an approximation method based on a plurality of iteration steps. Each point in a projection corresponds to a line in the reconstructed image. The projections are thus back-projected. This leads as a first step to a very crude approximation. Subsequently, the imaging process of transforming the Radon data is simulated for this approximation and then differences are calculated to do a back-projection again. For an optimization of the reconstructed picture, this iteration is repeated many times. The essential disadvantage of the iterative reconstruction is that the above iteration leads to extremely long calculation times.

The filtered back-projection method relies in principle on the Fourier-slice theorem describing a relationship of the Fourier transform of the Radon data and Fourier transformed image data. A general disadvantage of using the Fourier-slice theorem lies in the fact that an interpolation step in the reconstruction results in errors and artifacts which have a tendency even to increase with increasing space frequency. The capability of reconstructing images with fine details is limited. This disadvantage could be avoided by using detectors with high resolution only. However, the application of these detectors is limited in terms of dose burden, costs and data processing time. Another problem is related to the discretization of the Radon data from which the image data have to be reconstructed. To get an optimal filtered back-projection reconstruction it would be necessary to exactly match the projected irradiation rays with the sensor elements of the detectors. This is in general not the case. For this reason, uncertainties or smoothing effects from the reconstruction of Radon data by means of filtered back-projection algorithms are introduced. This drawback can in general not be overcome by filtered back-projection algorithms. It could be avoided by using the above mentioned iterative reconstruction but these are so computational expensive that they are not widely used in practical computed tomography.

The so-called Feldkamp algorithm or the advanced single slice reconstruction are methods that try to adapt the filtered back-projection algorithm to the case where the data are collected in helical computed tomography with fan or cone beam geometry which results in data points not evenly spread within the z-axis direction and the rays along which the projection and integrations take place are tilted against each other. According to the Fourier-slice theorem all possible rays have to be evaluated, because otherwise the error for high space frequencies would be larger. This leads to further uncertainties and unsharpness.

Generally, the conventional techniques allow that the unsharpness of the structure reconstruction can be reduced, but not avoided, by using algorithms with a higher need of computational power.

Current developments in computed tomography have provided so-called multi-slice-CT and CT-systems based on flat panel technology. These developments are suffering from two further major problems. First of all, the amount of data is very large, the reconstruction time for such an amount of data is too long or the computers needed to handle such data are too expensive. The second problem is scatter radiation. Scatter radiation becomes a bigger problem for larger radiated areas of the object. Conventional scatter reduction methods like grids do not have enough effect and the signal-to-noise ratios are anyhow already very small, which means that a further reduction of signal as resulting from inserting a grid would produce more artifacts and worse images. Additionally, assuming an oscillation of the grid relative to the detector to avoid grid lines, the rotation of the grid with the detector is very difficult in consideration of the rotation time of 0.5 s or less.

The above disadvantages are associated not only with the conventional CT imaging, but also with all available reconstruction methods related to Radon data. As an example, a practical reconstruction technique for neutron transmission imaging is not available at present. As a further example, the application of conventional ultrasound tomography e.g. in medicine is restricted to small or soft tissue objects since, the conventional reconstruction techniques require integrated projection data from the centre of the object to be investigated.

OBJECTIVE OF THE INVENTION

The objective of the invention is to provide improved methods of reconstructing image functions from Radon data, leading to an increased range of applications in non-destructive investigations and avoiding the disadvantages of the conventional reconstructing techniques. In particular, the objective of the invention is to provide reconstruction methods yielding image functions with reduced unsharpness and reduced artifacts even at high space frequencies. A further aspect of the objective of the invention is to provide an improved imaging method avoiding the disadvantages of the conventional imaging methods based on the collection of Radon data. Another objective of the invention is to provide improved devices for imaging a region of investigation by reconstructing measured Radon data. According to a particular aspect, the objective of the invention is to provide an imaging device which allows a reduction of an amount of energy input (e.g. radiation dose) and scattering effects within the region of investigation.

The above objectives are achieved with methods or devices comprising the features of patent claims 1, 16 and 27. Advantageous embodiments and applications of the invention are defined in the dependent claims.

SUMMARY OF THE INVENTION

According to a first general aspect of the invention, an (n+1)-dimensional image function $f$ representing a region of investigation (in the following: ROI) is determined from n-dimensional or less dimensional Radon data as a sum of polynomials multiplied with values of projection functions $p_\Theta(t)$ measured corresponding to a plurality of predetermined projection directions ($\Theta$) through the ROI.

In contrast to conventional reconstruction techniques using complex transformations or iterative calculations, the present invention provides the image function $f$ as an approximation of polynomial functions. The inventors have found that this approximation is determined just by the projection functions coming from the Radon data. As the result of an approximation (details see below, section 3.), the image function can be calculated using much less computational time than normally used by iterative reconstruction and comparable at least to that used by filtered back-projection algorithms.

The invention allows a fast reconstruction with very few artifacts and with resolution and noise properties directly combined to the number of measured energy quanta or the strength of the measured projection signals. Additionally the reconstruction does not use any interpolation to construct parallel data from fan beam data. The (n+1)-dimensional image reconstructed according to the invention does not suffer from resolution decrease due to the reconstruction itself and has less artifacts introduced by the reconstruction.

According to the present first aspect, the subject of the invention is a method of reconstructing the image function $f$ as such. The image function $f$ is a representation of the region of investigation (ROI). The values of the image function are determined by the local parameters or features of the ROI. The dimension of the image function depends on the dimension of the ROI, in particular on the number of parameters necessary for completely describing each point in the ROI. In the general case, the image function has (n+1) dimensions (n: natural number, $n \geq 1$). Accordingly, the term "image function" used herein does not necessarily refer to a visualized picture, but rather to a representation of the features of the real ROI or parts thereof, wherein the representation may be e.g. a numerical representation, a graphical representation or the like. The "image function" represents an approximation whose quality depends on the amount of data processed, but not on any interpolation. The approximation of the image function on a circle-shaped unit disc extending in the region of investigation is described in the following. The approximation on an ellipse-shaped disc can be done in an analogue way as outlined below.

The term "region of investigation" (ROI) used herein generally refers to an object under investigation or a part thereof. The ROI can be described as a 2- or higher dimensional entity as described above with reference to the image function. The ROI can be described by a smooth, continuous function without discontinuities like e.g. steps. It is an important advantage of the invention, however, that this condition of reconstructing a smooth ROI is fulfilled in all practical applications of the invention. Even a crack in a material under investigation does not represent an ideal discontinuity but rather a blurred step which can be reconstructed with the method of the invention.

The term "projection direction" used herein generally refers to the linear course of an energy input through the ROI in the (n+1)-dimensional space. In the 2- or 3-dimensional case, the projection direction can be defined by angles relative to a coordinate system used. If fan or cone beams are considered, the term "main projection direction" indicates the orientation of the central beam component in the fan or cone beam.

The Radon data measured at the ROI comprise a set of projection functions which have been determined corresponding to a plurality of predetermined projection directions running through the ROI. The n-dimensional data are collected with a certain number, which might in theory be infinite large, of "projections". These projections are characterized by integrating the interesting effect over one-dimensional lines. By measuring a sufficient number of these integrated "projections", important features of the object can be reconstructed from the Radon data.

The values of the projection functions generally are determined by the interaction (in particular attenuation, e.g. by absorption, scattering or reflection) of an energy input beam travelling through the ROI along the respective projection direction. While the projection function is a one-dimensional function, the entirety of projection functions corresponding to all available projection directions spans a space (Radon space) of higher dimensions. Generally, for reconstructing the (n+1)-dimensional image function, Radon data with n-dimensions are required. However, the reconstruction with Radon data having less dimensions is also possible.

The term "energy input beam" used herein refers to all types of a physical quantity, which travels along a straight line (or an essentially straight line) through the ROI while the energy carried is changed due to an interaction with the ROI. In particular, the term "energy input beam" covers electromagnetic radiation, particle radiation, sound waves or electrical current.

The term "Radon data" used herein refers not only to the data obtained by the above projections through the ROI, but also to data obtained by measuring an energy output obtained by reflection within the object investigated. These Radon data (or: Radon-like data) are obtained e.g. with the investigation of objects by the use of ultrasound waves. It is an essential advantage of the invention that the reconstruction of the image function can be implemented for Radon-like data.

According to a preferred embodiment of the invention, the image function $f$ has two, three or four dimensions with n being selected from 1, 2 or 3. The reconstruction of a 2-dimensional image function $f$ has the particular advantage in that the multiplication of the polynomials with values of the projection functions can be done with low computational power. The 2-dimensional image function represents e.g. an image of a disc section in an object under investigation. The reconstruction of a 3-dimensional image function has an advantage in that the calculation for reconstructing the image function can be obtained by a simple adaptation of the 2-dimensional case. The invention-based calculation for the 2D and the 3D case are based on mathematical operations which can be implemented in a very simple way, and with the possibility of precalculating a lot of values and store them within a computer or another data carrier, like e.g. a memory chip or chips. This means the number of operations will be greatly reduced as matrix elements (see equation 2.3 in section 3) can be precalculated.

Furthermore, the invention can be adapted with advantage to the 4-dimensional case wherein the ROI comprises three dimensions in space and time as the fourth dimension. As an example, the 4-dimensional image function is represented by a time sequence of a three-dimensional representation of an object under investigation e.g. a running motor engine, or an organ of a living organism, e.g. the heart. With regard to the reconstruction of 4-dimensional image functions, the invention offers essentially new applications of non-destructive imaging, e.g. with computer tomography. The high accuracy of reconstruction by the invention allows the reduction of energy input, e.g. X-rays which leads to a computing time reduction. Due to this computing time reduction obtained with invention, processes with relative high frequencies, e.g. the function of the beating heart, can be investigated in real time by an online imaging process.

According to a preferred embodiment of the invention, the image function $f$ is determined on the basis of sums of orthogonal ridge polynomials. With this embodiment, the convergence of the approximation of the image function is improved, so that the projection functions can be measured with a reduced number of samples allowing an advantageous reduction of energy input dose.

A measurement of projection functions is always associated with a discretization in practice. Due to the discretization of e.g. radiation sensor elements, any projection functions measured are composed of attenuation values according to single rays of energy or particle radiation. On the one hand, this discretization is advantageous for the sum calculation according to the invention. Furthermore, the method of the invention can be applied for reconstructing raw data obtained with conventional devices e.g. CT devices. On the other hand, the reconstruction method of the invention allows to achieve the above objective by using only certain discrete rays along which the integrated projection takes place. This is possible as the image function on a compact set can be approximated by the polynomials. The reconstructed image function is even an exact replica if the ROI is represented by a polynomial of degree less than the number of projection directions. The basic idea behind this is that continuous functions can be approximated accurately by polynomials.

Therefore, according to a particularly preferred embodiment of the invention the projection functions $p_\theta(t)$ comprise discrete projection profiles, wherein each discrete projection profile comprises projection values $\gamma(v,j)$ corresponding to a plurality of projection lines (j) with the same projection direction (v). An essential advantage compared with all conventional algorithms is that the invention-based method does not need all information gathered for conventional systems working with filtered back-projection. This leads immediately to the possibility of reducing the energy input, like e.g. the dose in CT-systems, or making imaging modalities like ultrasound useful for 3D-reconstructions.

The number and geometric features of the integrated projections for reconstructing the object properties to be investigated is selected in dependence on the particular application. In particular, the selection of the number and distances of the projection lines and the projection directions is done in dependence on the spatial resolution to be obtained, as an example by way of test measurements.

Generally, the polynomials used for reconstructing the image function are expressed with integrals on the ROI, e.g. on a disc section of ROI. The integrals can be calculated numerically as known in the art. However, according to a preferred feature of the invention, the integrals in the definition of the polynomials are discretized by a quadrature sum I. The quadrature sum I represents a discrete approximation of the integrals as outlined in the discussion of the mathematical background (see section 3.). The implementation of quadrature sums facilitates a direct processing of the measured data without any intermediate adjustment steps. Particularly preferred is the discretization of the integrals by the Gaussian quadrature sum, which has the important advantage in that the approximation of the integrals is more precise as a larger amount of polynomials is preserved despite of the discretization.

A feature of the reconstruction method is that the discrete projection values obtained with the same projection direction are measured such that the circumference of the unit disc in the ROI is divided by the projection lines into equal arc lengths. In this case, a polynomial matrix T can be constructed, the elements of which are sums of polynomials (see section 3). With this embodiment, the image function is approximated as a sum A of the discrete projection values multiplied by the corresponding elements of the polynomial matrix T added for all projections directions:

$$A_{2m}(f;x,y) = \sum_{v=0}^{2m} \sum_{j=1}^{n} \gamma_{v,i} T_{j,v}(x,y)$$

The elements of the polynomial matrix T are calculated as given by equation 2.1 given below (section 3.2).

The essential advantage of this embodiment consists in that the image function reconstruction is reduced to a simple double sum calculation which allows a reduction of calculation time.

The number of calculations and its type allows fast evaluation of the above mentioned double sum due to the fact that no re-binning is needed and a lot of calculations can be done beforehand, because the matrix used is in general only depending on the geometric conditions of the data collection. This means it can be precalculated and stored within the reconstruction computer or another data carrier.

Another important advantage of approximating the image function on the basis of the above matrix multiplication consists in that the polynomial matrix T allows an adaptation to particular conditions of measuring the projection values. The inventors have found that the conditions of measuring the projection functions directly influence the elements of the polynomial matrix. In particular, a system calibration due to non-homogenous radiation of the tube or non-linear response of the detector elements can be used as calibration properties and put into the polynomial matrix T to improve the image quality by online calibration. The improvement comes from the fact that various interpolations for conventional reconstruction schemes are no longer needed. Therefore, with a preferred feature of the invention, a calibration of the polynomial matrix T is introduced for providing an adjusted polynomial matrix T*. As long as the conditions of measurement are not amended, the adjusted polynomial matrix T* can be used for reconstructing the image function of different objects.

Preferably, at least one of an energy distribution function of an energy generator device, a sensitivity distribution function of a detector device used for measuring the projection functions, and a scattering function of the object is used for constructing a calibration matrix β. The adjusted polynomial matrix T* can be obtained from the polynomial matrix simply by multiplication by the calibration matrix.

$$T^* = \beta^* T$$

The above functions illustrating the energy and sensitivity distributions and the scattering properties of the object are obtained from a calibration measurement and possibly by theoretical considerations.

A calibration measurement can be implemented e.g. in CT devices with a homogenous sphere made of PMMA for measuring the energy distribution of the X-ray source (Heel-effect) and the sensitivity distribution of the sensor elements. The theoretical estimation of the scattering function as it is known from conventional techniques can be used for calibration. However, a strong disturbance due to scattering can be avoided by the invention if the projections are measured with straight pencil or needle beams having a reduced scattering effect (see below).

The polynomial matrix T used for approximating the image function has an essential advantage in that the elements of the polynomial matrix depend on measurement geometry only. In particular, the elements of the polynomial matrix T depend on the number and distances of the projection lines and the election of projection directions only. Therefore, the polynomial matrix needs to be calculated one time only for a pre-determined set of geometric measurement conditions. The same is true for the adjusted polynomial matrix T* which can be used for multiple measurements as long as the measurement conditions as e.g. the energy or the sensitivity distributions are not changed.

Preferably, at least one of the polynomial matrix T and the calibrated polynomial matrix T* is stored in a storage connected with or contained in a measuring device for measuring the projection functions. Particularly preferred is the storage of the polynomial matrix T and/or the adjusted polynomial matrix T* or a plurality of matrices corresponding to different conditions of measurement before a process of measuring the projection functions.

According to a preferred embodiment of the invention, the reconstruction method is connected with the measurement of the projection functions, wherein the process of measuring the projection functions firstly comprises the step of arranging an object to be investigated in the measuring device for adjusting the geometrical conditions of the measurement. Subsequently, the object is subjected to an energy input directed along the plurality of predetermined projection directions (Θ). For each of the energy inputs, the projection functions $p_\theta(t)$ are measured.

The combination of the measurement with the reconstruction as provided by this embodiment represents an essential development compared to conventional techniques. Due to the high reconstruction speed, the image function can be determined immediately after the measurement along a full circle of projection directions. The measurement of the data and the arrangement of the object in the measuring device can be optimized during the scanning to achieve better result.

According to a further modification of the invention, helical projection data can be processed for obtaining 2- or 3-dimensional image functions. The inventors have found that the conventional algorithms for adapting a reconstruction method to measurements with inclined disc sections can be applied to the reconstruction method of the invention. Accordingly, with a further embodiment of the invention, at least one of the object and the measuring device is translated in a predetermined direction, e.g. perpendicular to the projection directions (Θ) during the step of subjecting the object to the energy input for obtaining the helical projection data.

According to a further preferred embodiment of the invention, the sum of polynomials is subjected to a predetermined multiplier function which reduces the contributions of polynomials of higher degrees according to the multiplier function. Advantageously, this multiplier function allows a reduction of artifacts and improves the approximation of the image function. The multiplier function has the effect of a filter with a smooth transfer function filtering polynomials of the higher degrees in the orthogonal basis considered. In contrast to conventional techniques, this filter is not a traditional filter in the Fourier domain.

Generally, the invention can be used for reconstructing (n+1)-dimensional data from Radon data or Radon-like data in n or less dimensions. It is an essential advantage of the invention, that this reconstruction can be used in various applications like many applications in medical imaging, for example CT, PET, SPECT, gamma-camera imaging etc. However, there are a lot more possible applications like ultrasound tomographic imaging, light tomography, any multidimensional imaging for industrial testing or biological research and so on. Preferably, the image function f is determined from Radon data measured in an X-ray computer tomography (CT) device, an ultrasound tomography device, a PET imaging device, a Gamma-ray imaging device, a SPECT imaging device, a neutron based transmission detection system, or an electrical impedance tomography device.

According to a second general aspect of the invention, an imaging method for imaging the ROI is provided, wherein a plurality of straight energy input beams is directed at predetermined projection directions through the ROI and associated projection functions $p_\theta(t)$ are determined comprising attenuation values measured along the projection directions. According to the invention, the projection functions $p_\theta(t)$ are subjected to a reconstructing method according to the above first aspect of the invention. In contrast to any comparable conventional tomography imaging method, the imaging method of the present invention allows the direct processing of the measured projection data without re-binning. The image function can be calculated directly from the raw data obtained with an imaging device.

Depending on the application of the imaging method, further procedural steps for providing the requested image information in an appropriate format may follow. Preferably, an approximation of the image function is represented as a visualized image, e.g. with at least one 2- or 3-dimensional picture or a corresponding video representation (motion picture). Alternatively, the image function can be subjected to further image processing, e.g. for automatically detecting predetermined features. Advantageously, prior art image processing methods can be applied on the image function determined according to the invention. The provision of the visualized image comprises the step of calculating visualizations of the object, e.g. by converting the values of the image function into grey values.

The imaging method of the invention can be applied for any collection of Radon data obtained from any type of energy input acted on the object. In particular, there is no dependency on the distribution function describing the shape of the energy input generated by a particular energy generator. As an example, the imaging method can be implemented with many types of radiation sources that generate electromagnetic or particle radiation with a certain distribution.

According to a preferred embodiment of the invention, the energy input beams are fan beams or cone beams. The irradiation of the ROI with a radiation source having a fan or cone beam characteristic has the particular advantage in that conventional imaging devices, like e.g. CT or SPECT devices can be used for implementing the imaging method of the invention.

The terms "continuous fan beam" or "continuous cone beam" used herein refers to fan or cone beams with a smooth radiation field according to the distribution characteristic of the radiation source. The terms "discrete fan beam" or "discrete cone beam" used herein refers to fan or cone beams with a discretized radiation field according to the distribution characteristic of the radiation source shaped with a space filter, e.g. a mask.

According to a preferred modification, only predetermined fan or cone beam components are used for constructing the discrete projection profiles mentioned above, wherein all fan or cone beam components contributing to one discrete projection profile have the same projection direction. The selection of the fan or cone beam components facilitates the signal processing as outlined above.

According to an alternative embodiment of the imaging method, the energy input beams are formed as pencil beams (or: needle beams). Advantageously, available particle beam sources, like e.g. neutron sources can be used for implementing the imaging method of the invention. Another advantage is the capability of direct measurement of discrete projection profiles according to the direction of the pencil beams.

Alternatively, if a plurality of pencil beams having the same projection direction is generated in a continuous mode by a moving radiation source, discrete projection profiles can be constructed by selecting certain beam components as outlined above.

If a plurality of sets of discrete fan or cone beams are directed through the ROI, discrete projection profiles can be constructed comprising attenuation values of beam components having the same projection direction but being contained in different sets of discrete fan beams. This feature allows a simple adaptation of conventional imaging devices to the reconstruction method of the invention.

Preferably, the fan beam components or the discrete pencil beams are provided by combining a radiation source with a source mask that shapes the initial radiation characteristic of the source according to the requested straight beam components.

According to a further preferred embodiment of the invention, the projection directions ($\Theta$) are set subsequently by using a movable radiation source being rotated around the subject. Advantageously, the rotatable radiation source allows a free adjustment of projection directions in dependence on the particular practical application. If the projection directions ($\Theta$) are set in at least one common plane crossing the region of investigation, the construction of the projection profiles is facilitated. However, the inventors have found that the projection directions ($\Theta$) can be set in varying inclined planes crossing the ROI for obtaining helical projection data. In this case, 3-dimensional images of the ROI can be obtained.

An essential advantage of the imaging method of the invention consists in that there is no restriction with regard to the object to be investigated or the size thereof. As the invention allows an essential reduction of radiation dose, preferably radiation sensitive objects like biological organisms or parts thereof can be investigated. On the other hand, non-destructive investigations in all fields of material science or technology, in particular for imaging solid or fluid materials and in particular technical devices (e.g. engines or mechanical components, like e.g. components in construction technique) are possible. It is a particular advantage of the invention that simply by selecting appropriate geometric conditions of the energy input, in particular by selecting the projection directions and the distances of the projections contributing to one projection profile, the imaging method can be adapted to the object to be investigated. For particular purposes, like security checks at airports, a low resolution can be set. On the other hand, Radon data collected on geological or even astronomical dimensions can be reconstructed and further processed with the methods of the invention.

The invention-based method provides a reconstruction that is superior to other reconstruction methods because the resulting resolution of the pixels of the object is only determined by the number of rays used for the imaging process. That means that one can reduce X-ray dose e.g. in CT by far if the object to be investigated is small as for children or the resolution needed is very low like for example the potential use of CT-scanners at airports to avoid terrorist attacks. This direct relation is not valid in conventional devices due to the problems raised by interpolation. Because the invention-based technique would only need certain X-ray rays through a human body which would result in a dose smaller than any dose gathered during even a short flight in a commercial aircraft, so that weapons or explosive material even within a body could be detected without too much X-ray exposure. This might allow new and better quality of security examinations.

According to a third general aspect of the invention, an imaging device for imaging the region of investigation comprises a measuring device for measuring projection functions $p_\Theta(t)$ corresponding to a plurality of predetermined projection directions ($\Theta$) through the ROI, wherein a reconstruction circuit connected with the measuring device is adapted for reconstructing an image function $f$ as a sum of polynomials multiplied with values of the measured projection functions $p_\Theta(t)$.

Preferably, the reconstruction circuit is adapted for reconstructing the image function $f$ with a method according to the above embodiments of the invention. Accordingly, the reconstruction circuit comprises a summation circuit for determining the image function $f$ as the above sum of projection values.

Preferably, the imaging device according to the invention comprises an energy generator device for directing an energy input beam into or through the object under investigation and a detector device for measuring the projection functions $p_\Theta(t)$. The energy generator device comprises at least one energy input source and a source carrier, wherein the energy input source is movable on the source carrier relative to the object.

If the source carrier has a ring shape and the energy input source is able to be rotated around the object, the setting of projection directions is facilitated. Furthermore, the energy input source can be made to be movable along a helical path relative to the object.

Preferably, the detector device comprises at least one sensor array with sensor elements for detecting attenuation values representing the attenuation of energy input corresponding to the plurality of predetermined projection directions.

Advantageously, the invention can be implemented with conventional energy or particle radiation sources. As an example, a fan or cone beam source can be used as the energy input source for emission of electromagnetic radiation. Alternatively, a pencil beam source for emission of electromagnetic or particle radiation can be used.

According to a particularly preferred embodiment of the invention, the radiation source of the imaging device carries a source mask for shaping an energy distribution function of the radiation source and for providing a plurality of straight pencils beams within the radiation field of the radiation source. Preferably, the source mask is movable with the radiation source. If the source mask is detachable from the radiation source, the geometric conditions of irradiation can be adapted with advantage to various applications.

According to a further preferred embodiment of the invention, the source mask comprises a plate made of a shielding material and containing through holes allowing a transmission of beams components with a predetermined orientation.

As an alternative measure for orienting the beams components, the energy generator device comprises a plurality of fixed frame masks for shaping an energy distribution function of the energy input source. The frame masks are fixed on the source carrier at predetermined positions, preferably spaced with equal arc lengths.

According to a further preferred embodiment of the invention, the source carrier comprises a ring-shaped shield containing the frame masks, the ring-shaped shield shielding the energy input source at positions other than the positions of the frame masks. This embodiment provides an essential advantage in that the radiation dose and the scattering in the object can both be reduced.

In contrast to conventional devices, the detector device can comprise a plurality of fixed frame sensors for detecting attenuation values representing the attenuation of energy input corresponding to the plurality of predetermined projection directions. The frame sensors are fixed on the source carrier at predetermined positions, preferably adjacent to the frame masks on radiation windows in the ring-shaped shield.

Further subjects of the invention are digital storage media or computer program products with electronically readable data comprising a sum of polynomials, in particular the polynomial matrix T. Such data are capable of interacting with a calculation unit in the imaging device of the invention and/or of conducting a method according to the invention, as well as interacting and conducting a computer program with a program code for conducting the method according to the invention, when the program is running on a computer.

BRIEF DESCRIPTION OF THE DRAWINGS

Further details and advantages of the invention are described in the following with reference to the attached drawings, which show.

EMBODIMENTS OF THE INVENTION

The invention is described in the following text with reference to the application in computer tomography (sections 1., 2.1). It is emphasized that the invention can be implemented in an analogous way with the other applications mentioned above (examples in section 2.2). Furthermore, the following description of the preferred embodiments mainly refers to the data collection and the data processing. Details of the CT devices used for implementing the invention are not described as far as they are known from conventional CT devices.

Figure 1:
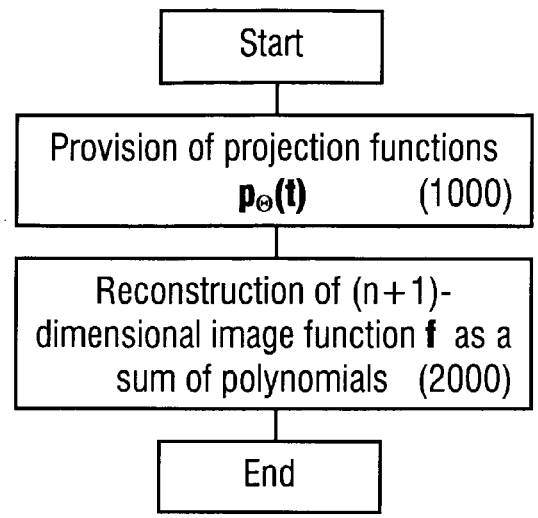
FIG. 1 a flow chart illustrating the basic steps of a reconstruction method according to the invention.

The basic principles of reconstructing an image function representing an ROI are described in the following text with reference to FIGS. 1 and 2. The imaging method of the invention as well as details of imaging devices used according to the invention will be described with reference to FIGS. 3 to 14.

1. Basic Principles of Reconstruction and Imaging (1.1) According to FIG. 1, the basic steps of a reconstruction method according to the invention comprise the provision of projection functions representing Radon data (step 1000) and the reconstruction of an image function as a sum of polynomials multiplied with values of the projection functions (step 2000). The reconstruction is based on the remarkable result of the inventors according to which a partial sum of an expansion of a function in an orthogonal basis of polynomials can be expressed in term of the Radon projections. Details of this relationship are illustrated below (section 3.1).

The practical implementation of the reconstruction in particular depends on the field of the application and the desired level of approximation. On the basis of quasi-continuous projection functions (discretized by sensor elements only), the above partial sums can be calculated directly. If discrete projection profiles are used for determining the image function, an approximation on the basis of the Gaussian quadrature or in particular on the basis of the polynomial matrix T is preferred. In the following, reference is made to the preferred embodiment using the polynomial matrix T. The skilled person will implement the reconstruction on the basis of a quasi-continuous function in an analogue way.

The following consideration refers to the reconstruction of a 2-dimensional image function from 1-dimensional Radon data (1-dimensional projection functions). This corresponds to the simplest case of imaging based on data resulting from rays in one single slice from which this particular slice is to be reconstructed. The reconstruction of higher dimensional image functions will be implemented in an analogue way as outlined in section 3.

For the illustrated embodiment, the ROI is located within a 2-dimensional plane. The orthogonal x- and y-direction of a Cartesian coordinate system are defined in this plane, while the orthogonal z-direction is directed perpendicular relative to the x-y-plane. Directing energy input beams into the ROI means that the respective energy input (e.g. radiation) is travelling along a projection line v in the ROI plane. If the ROI plane is perpendicular relative to the z-direction, all projection lines having the same projection direction (in the 2-dimensional case: projection angles) are parallel to each other.

If the ROI plane is inclined as e.g. with helical measurement geometry, the projection lines are not necessarily parallel to each other. In this case, measured values according to predetermined projection lines which are parallel to each other can be selected from the raw data.

Figure 2:
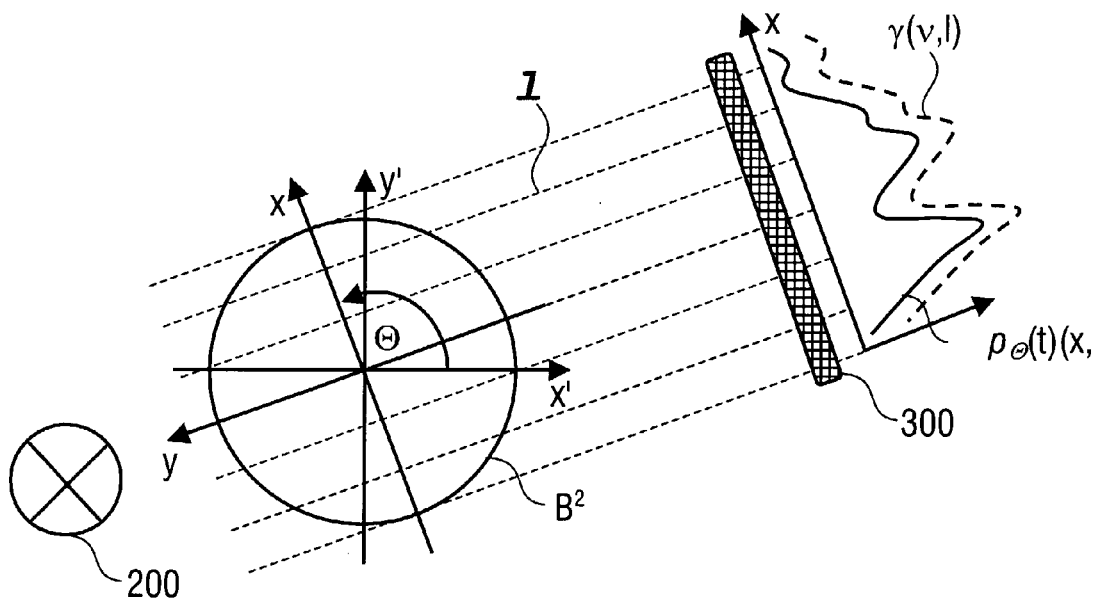
FIG. 2 a diagram illustrating the collection of Radon data.

FIG. 2 illustrates the collection of one particular projection function $p_\Theta(t)$ corresponding to a certain projection direction v. A plurality of parallel projection lines 1 (dashed lines) run through the unit disc $B^2$ according to the current projection direction, which represents a rotation by the projection angle $\Theta$ relative to a start condition (x', y'). The radiation from a radiation source 200 (illustrated schematically) travels along the projection lines 1 through the ROI containing the unit disc. Due to the integrated interaction along the projection line, the radiation is attenuated. The attenuation is measured with a detector device 300 (illustrated schematically) comprising a linear array of sensor elements. The signals of the sensor elements represent the projection function $p_\Theta(t)$ illustrated in the right part of FIG. 2.

In the illustrated 2-dimensional case, the Radon data $R_{\phi v}$ comprise the plurality of 1-dimensional projection functions measured according to a plurality of different projection directions. The number of projection directions is selected in dependence on the resolution requested. According to the invention, any smooth function representing the features of a structure in the ROI can be approximated by polynomial functions. Using the invention based procedure this approximation is done by orthogonal polynomials of several variables. The details of the calculation are given in the section 3. According to the general expressions 1.4 and 1.5 in section 3.1, the image function can directly be calculated as a partial sum $S_{2m}$ from the measured Radon data $R_{\phi v}$ based on projection functions $p_\Theta(t)$.

$$S_{2m}(f; x, y) = \sum_{v=0}^{2m} \frac{1}{\pi} \int_{-1}^{1} R_{\phi v}(f, t) \Phi_v(t; x, y) dt$$

Discrete projection profiles γ (illustrated with a dashed line in FIG. 2) are determined comprising the attenuation values according to a plurality of projection lines 1. According to the general expression 2.1 in section 3.2, the approximation of the image function can be directly calculated as a double sum $A_{2m}$ from the measured projection values γ.

$$A_{2m}(f; x, y) = \sum_{v=0}^{2m} \sum_{j=1}^{n} \gamma_{v,t} T_{j,v}(x, y)$$

As the result, the sums $S_{2m}$ or $A_{2m}$ directly provide an approximation to the image function f to be obtained.

Figure 3:
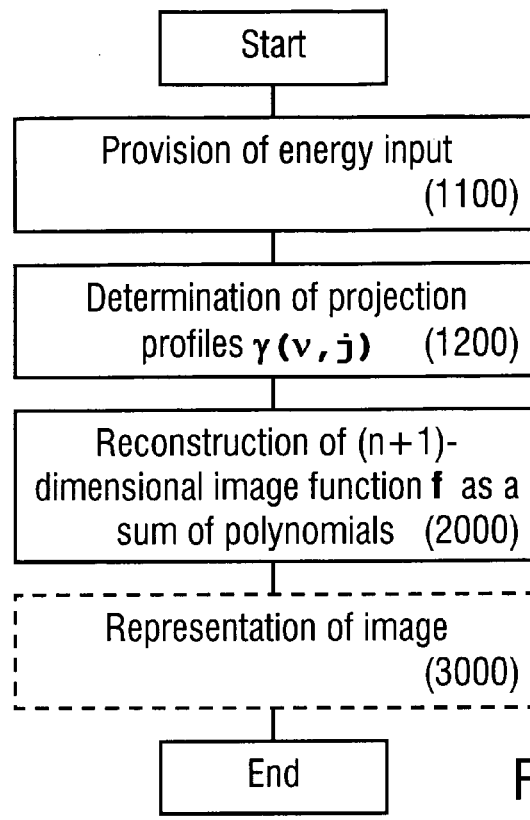
FIG. 3 a flow chart illustrating further steps of the reconstruction method of the invention.
Figure 4:
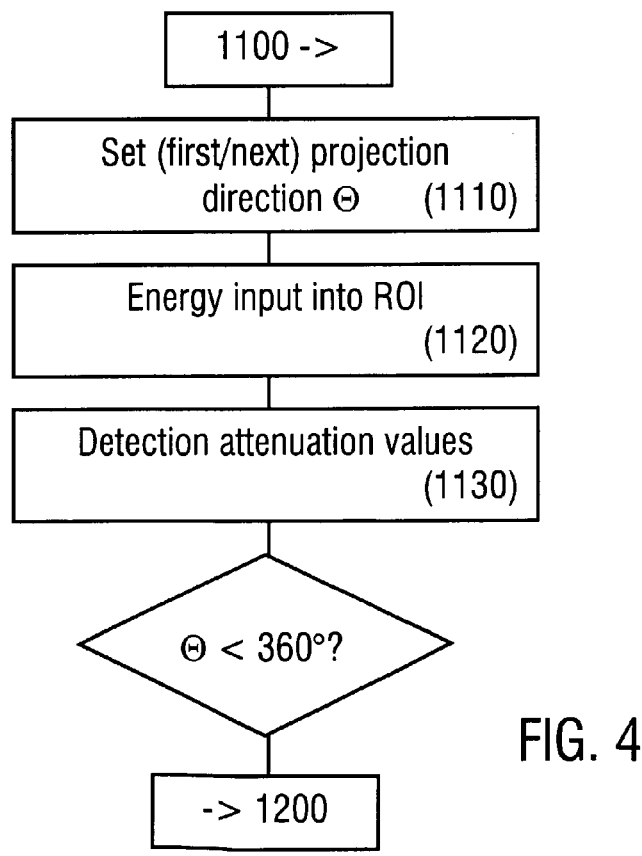
FIG. 4 a flow chart illustrating the setting of projection directions in an imaging method of the invention.

(1.2) The basic steps of an imaging method according to the invention are illustrated in FIGS. 3 and 4. According to FIG. 3, the projection functions, in particular the discrete projection profiles, are determined by the steps of directing an energy input beam into or through the ROI (step 1100) and the determination of the projection profiles (step 1200). Subsequently, the image function f is reconstructed (step 2000) and (if applicable) the image function f is represented as a visualized image (step 3000).

Figure 12:
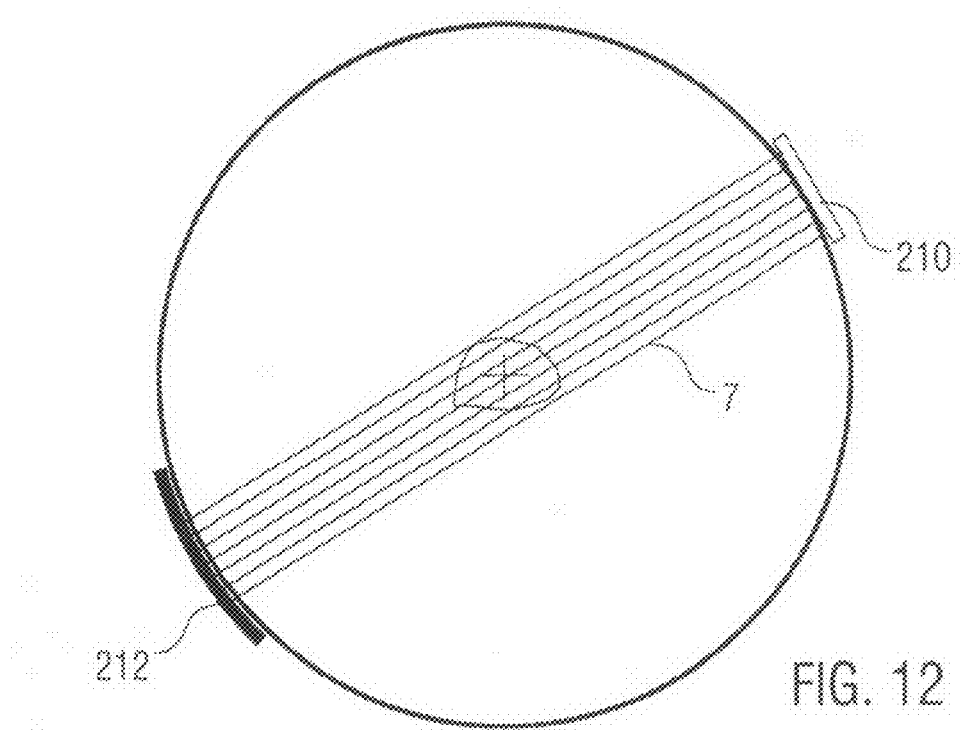

Step 1100 comprises the step of directing the energy input beams into the ROI. This is implemented e.g. with an available radiation or particle source (see below) being directed or focused to emit beams in the plane of the ROI. With step 1200, the projection profiles are determined. This comprises a direct measurement, if all beams with the same projection direction are directed through the ROI simultaneously, as shown in FIG. 12. Alternatively, the discrete projection profiles are constructed from measurements with fan or cone beam components as illustrated below with reference to FIG. 7. In this case, attenuation values measured at different positions of the radiation source are arranged in discrete projection profiles such that all attenuation values being measured with the same projection direction contribute to the same projection profile.

Further details of step 1110 are illustrated in FIG. 4. At the beginning of the measurement, a first projection direction $\Theta$ is set (step 1110) and selected in dependence on the operation condition of the imaging device used in practice. Setting the projection direction means that the energy generator device (e.g. radiation source) and the detector device are arranged such that a connecting line between both devices runs through the ROI. In particular imaging devices, e.g. based on the measurement of ultrasound waves, both the ultrasound generator and the detector device are arranged on the same side of ROI. With step 1120, the energy generator is activated so that an energy input beam is travelling through or at least into the ROI. Accordingly, with step 1130, the detection of attenuation values is conducted with the detector device.

After step 1130, a decision is made whether the full circle has been scanned. If not, the next projection direction is set (step 1110). Otherwise, the projection profiles are determined according to step 1200 in FIG. 3.

2. Practical Implementation of the Invention 2.1 Computer Tomography

Figure 5:
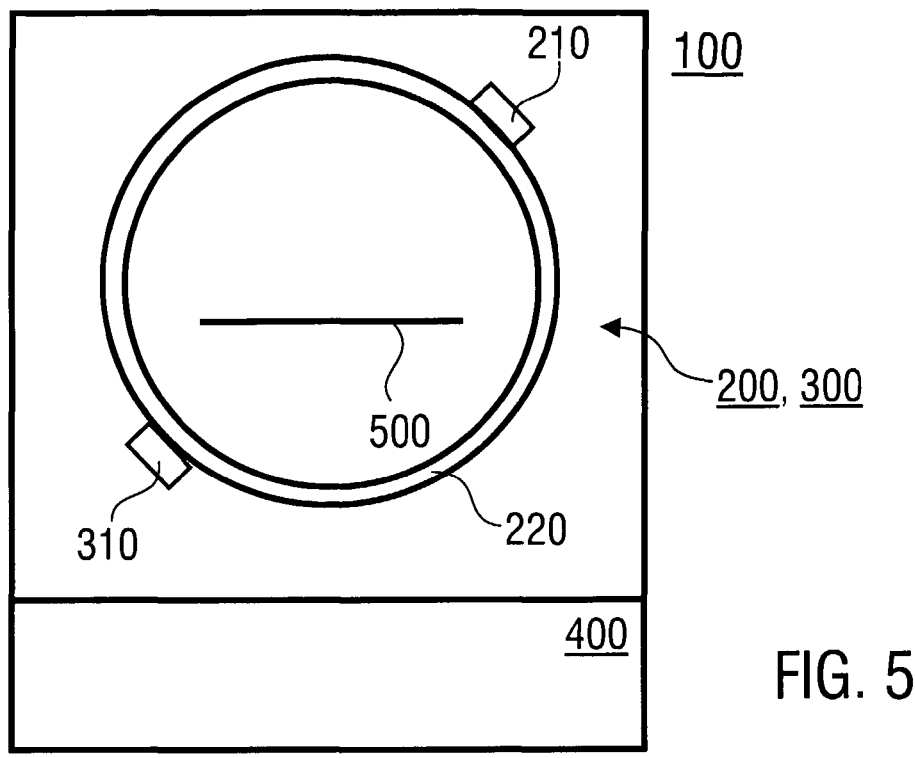
FIG. 5 a schematic representation of an embodiment of an imaging device according to the invention.

FIG. 5 schematically illustrates an embodiment of the imaging device 100. The imaging device 100 comprises the measuring device with the energy generator 200 and the detector device 300 and the reconstruction device 400 being connected with the measuring device. Furthermore, a holding device 500 is provided, which is e.g. a carrier table as it is known from CT systems or any other carrier or substrate holder for arranging an object under investigation in the measuring device and for adjusting the geometry of the object relative to the energy generator 200 and the detector device 300. Further components like a control device, a display device etc. (not shown) are provided for as they are known per se from prior art devices.

The energy generator 200 comprises an energy input source 210, like e.g. a movable X-ray tube arranged on a source carrier 220 (e.g. a guide rail) as it is known from conventional CT devices. The detector device comprises a sensor array 310 which is movably arranged on the source carrier 220 in opposite relationship relative to the energy input source 210. With this structure, the projection direction through the ROI (parallel to the plane of drawing) can be set by rotating the combination of components 210, 310 around the holding device 500.

The source carrier 220 is illustrated as a circle allowing a rotation of the energy generator 200 and the detector device 300 around an object. According to a modification, the source carrier can have an ellipse shape or another shape. This can represent an advantage in terms of an adaptation to the geometry of the object to be investigated.

Figure 6:
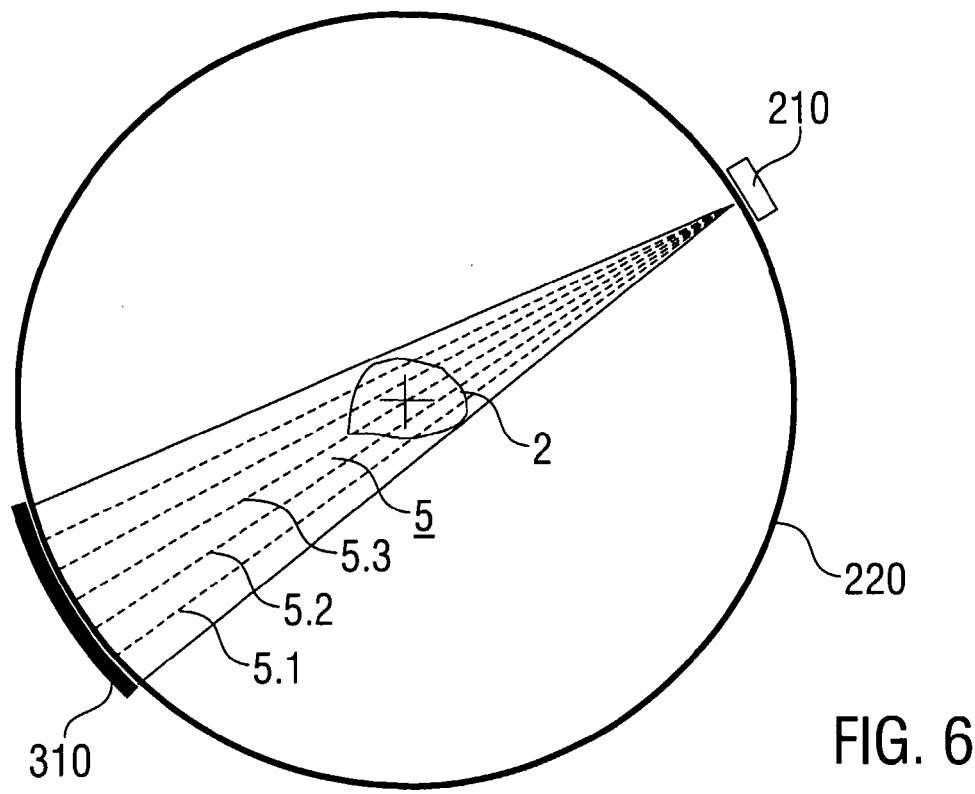
FIGS. 6 to 8 further illustrations of directing fan beams or pencil beams through an object under investigation.

If the invention is applied in computer tomography, the imaging device 100 is structured like a current medical CT-system. Directing a continuous fan or cone beam 5 through ROI 2 in a CT system for collecting projection data is schematically illustrated in FIG. 6. The CT-system (not completely illustrated) includes the ring-shaped source carrier 220 in which the X-ray tube (radiation source 210) and the detector device 310 are rotating in a way that the whole system can finish a complete turn within e.g. 0.3 to 0.5 s. The detector device 310 consists e.g. of 1 to 64 rows of sensor elements (if it is more than one row it would be called a multi-slice-CT) and approximately 700 and 1000 sensor elements per row. Within each single turn the data are read about 1000 times. The object under investigation, e.g. a patient, is moving through this CT-ring, lying on a patient table, that is moving continuously. By this method a so-called helical or spiral CT data set can be gathered, because the data that are collected are located on a spiral net (see FIG. 14).

The detector device 310 is a linear or 2-dimensional array of sensor elements being arranged on a spherical reference surface adapted to the radius of the CT-ring. It is an essential advantage of the invention that the provision of a spherical detector device is not necessarily required. Alternatively, a plane detector device with a straight (1-dimensional) or a plane (2-dimensional) arrangement of sensor elements can be used. Although the sensor elements on a plane detector device would not sense attenuation values according to the equally spaced arc length positions mentioned below, this would not influence the quality of the reconstruction according to the invention. Due to the fixed geometrical relationship between the arrangement of sensor elements on a plane detector device compared with the arrangement on a spherical detector device at the same position, the above approximation of the image function can be adapted. Such a simple adaptation is impossible with the prior art reconstruction techniques which would require an extra interpolation step for a plane detector device.

For the invention-based reconstruction method, not all possible rays resulting from the geometry of the tube and the detector geometry (current detector elements have a size of 0.5 to 1.0 mm) are needed for the reconstruction. This is a major difference to conventional filtered back-projection algorithms for which as many detector elements as possible have to be read out, because the more detectors are read out per unit square meter, the smaller is the necessity of doing interpolations and therefore the smaller is the blurring implicated by the reconstruction. For the invention-based reconstruction method only certain rays are needed. These rays are adjusted in a way that the correct number of parallel beams is achieved for the imaging conditions. By increasing the number of rays and projections a higher resolution can be achieved, that means the number of pixels which can be reconstructed free of artifacts can be increased. There is no additional blurring due to the reconstruction.

The selection of parallel beam components can be done with a conventional CT-system as outlined in the following. Reference is made to fan beams, while cone beams are handled in an analogue way. Each fan beam 5 as illustrated in FIG. 6 represents a bundle of fan beam components 5.1, 5.2, 5.3 .... Each of the fan beam components 5.1, 5.2, 5.3 ... can be considered as a straight pencil beam. While these pencil beams as such do not have the same projection directions, the determination of the discrete projection profiles according to step 1200 in FIG. 3 follows a concept which is illustrated in FIG. 7.

Figure 7:
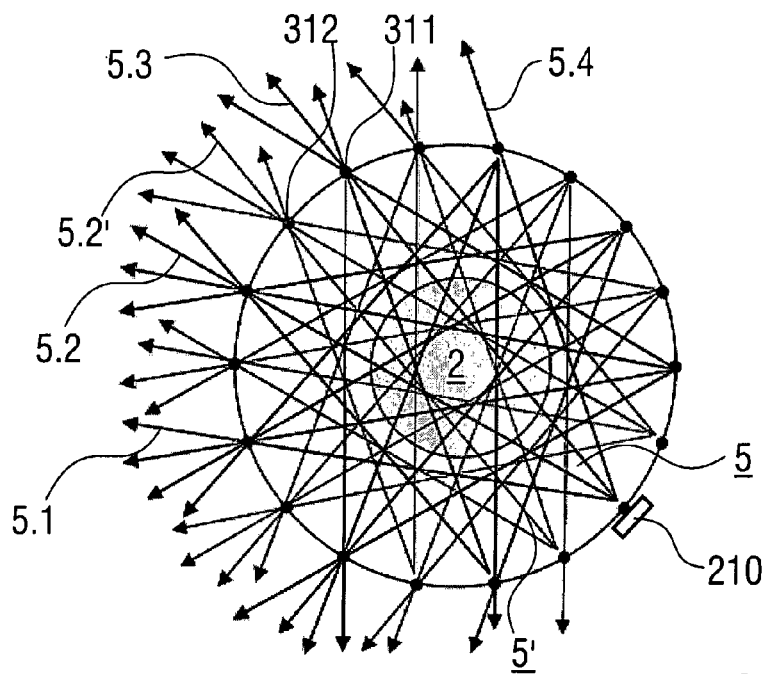

FIG. 7 illustrates a plurality of fan beams (e.g. fan beam 5) each of which comprising the fan beam components 5.1 to 5.4. In practice, the number of beam components may be essentially higher than shown in FIG. 7 (see below, description of FIGS. 8 and 9). Furthermore, the geometry of the fan beam can be modified so that fan beam components intersecting the centre of ROI 2 are provided. Furthermore, fan beam components which do not intersect the ROI 2 can be omitted, e.g. by source geometry or masking. For a first main projection direction corresponding to the illustrated position of the radiation source 210, the fan beam component 5.3 runs through ROI 2 as a straight pencil beam being detected at the sensor element 311 of the detector device 310 (detector array). For obtaining an attenuation value of another projection line parallel to the fan beam component 5.3, the fan beam component 5.2' of the fan beam 5' radiated at a changed position of the radiation source 210 is detected at the sensor element 312. With an appropriate selection of the sensor element positions and the radiation source positions, in particular with an arrangement of these positions spaced with equal arc lengths, attenuation values measured with fan beam components having the same projection and in particular being parallel can be used for constructing the discrete projection profile.

This concept can be used for the reconstruction of image functions from projection data collected with a conventional CT device according to FIG. 6. As the positions of the radiation source 210 and the detector device 310 and the positions of the sensor elements 311 within the detector device 310 are known from each selected projection direction, the attenuation values for constructing the discrete projection profiles can be simply selected from the collection of raw data obtained with the CT device.

Figure 8:
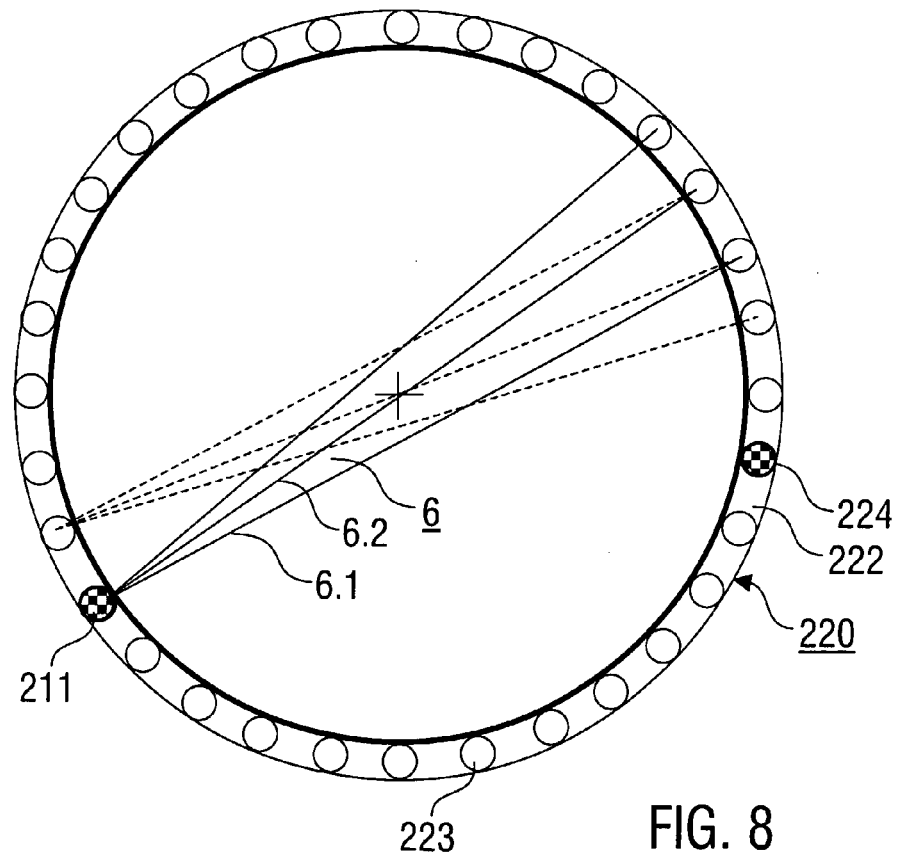
Figure 9:
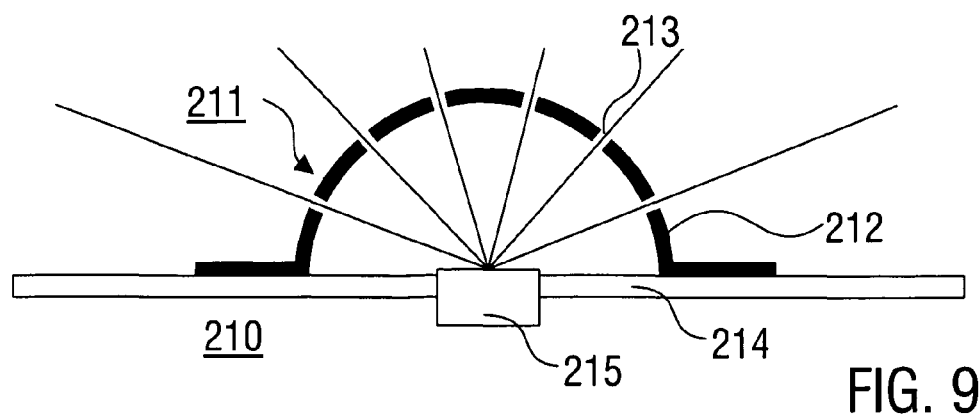
FIGS. 9, 10 schematic illustrations of an embodiment of beam shaping masks used according to the invention.
Figure 10:
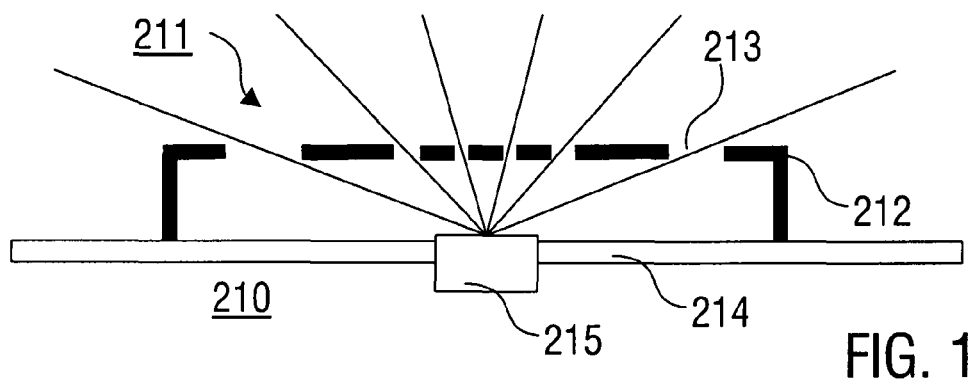

This selection of raw data can be automated by replacing the continuous fan beam illustrated in FIG. 6 by a discrete fan beam illustrated in FIGS. 8 to 10. Generally, the discrete fan beam can be generated with a radiation source emitting a continuous fan (or cone) beam combined with a mask that allow only certain components of the continuous fan beam being transmitted through. These components can be considered as straight pencil beams. The function of the mask can be fulfilled by the source mask being positioned on the radiation source and being movable therewith, or by a plurality of fixed frame masks being arranged on the source carrier or a ring-shaped shield attached thereto. The embodiment using the source mask is preferred as the source mask can be detachable and be positioned on the radiation source. In dependence on the object under investigation, a source mask with the appropriate number and spacing of straight beam components can be selected from a set of different source masks and attached to the radiation source.

According to FIG. 8, the discrete fan beam 6 comprising fan beam components 6.1, 6.2, ... is generated with a radiation source 210 equipped with the source mask 211. The source mask 211 is adapted for shaping the energy distribution function of the radiation source 210. To this end, the source mask 211 comprises a shielding plate 212 for example made by tungsten with through holes 213 as schematically illustrated in FIGS. 9 and 10. The shielding plate 12 can have a spherical shape (FIG. 9) or a plane shape (FIG. 10) or any other appropriate shape adapted to the schematic conditions of the imaging device. The through holes 213 are arranged such that the projection lines starting at the radiation source cross the circle in line with the detector elements on at predetermined positions, in particular, they can be arranged with an equal arc length spacing.

The source mask is fixed to the radiation source (e.g. X-ray tube), in particular to a frame 214 of an output window 215 of the radiation source 210 by a detachable fixing element, like e.g. a clip element or a snap connection. The discrete fan beam 6 comprises e.g. 200 straight fan beam components.

With the discrete fan beam generated by the mask illustrated above, the signals from the sensor elements of the detector device detecting the attenuation along the corresponding projection lines are read-out at certain positions of the radiation source and the detector device only. The read out positions are those arc length positions on the ring-shaped source carrier, which fulfill the condition of selecting fan beam components with the same projection directions as illustrated in FIG. 7.

For reducing the radiation or particle exposure of the object under investigation, it is preferred to direct the energy input (e.g. radiation) into the object under investigation only at the above read-out positions, namely the sensor element signals are read out only when the combination of a radiation source and the detector device is oriented to the suitable positions. During the movement of the radiation source, this condition is fulfilled for certain times and/or for certain arc length positions of the radiation source. As long as the read-out condition is not fulfilled, the radiation source can be shut off or shielded. Shielding the radiation source is preferred for keeping radiation conditions stable.

The shielding function can be fulfilled by a ring-shaped shield 222 which is schematically illustrated in FIG. 8 with a plurality of radiation windows 223. The ring-shaped shield 222 can be detachably fixed to the source carrier 220 for adapting the geometric properties of the shield 222 to the practical application and in particular to the mask used. As an example, the ring-shaped shield 222 comprises 201 radiation windows 223 each having a diameter of 6 mm (with a diameter of the CT-ring: 80 cm).

The source masks 211 described above can be omitted if each radiation windows 223 of the ring-shaped shield 222 is provided with a frame mask 224 which is illustrated in FIG. 8 as an example only. In fact, the source frame masks 211, 224 need not be provided simultaneously.

Figure 11:
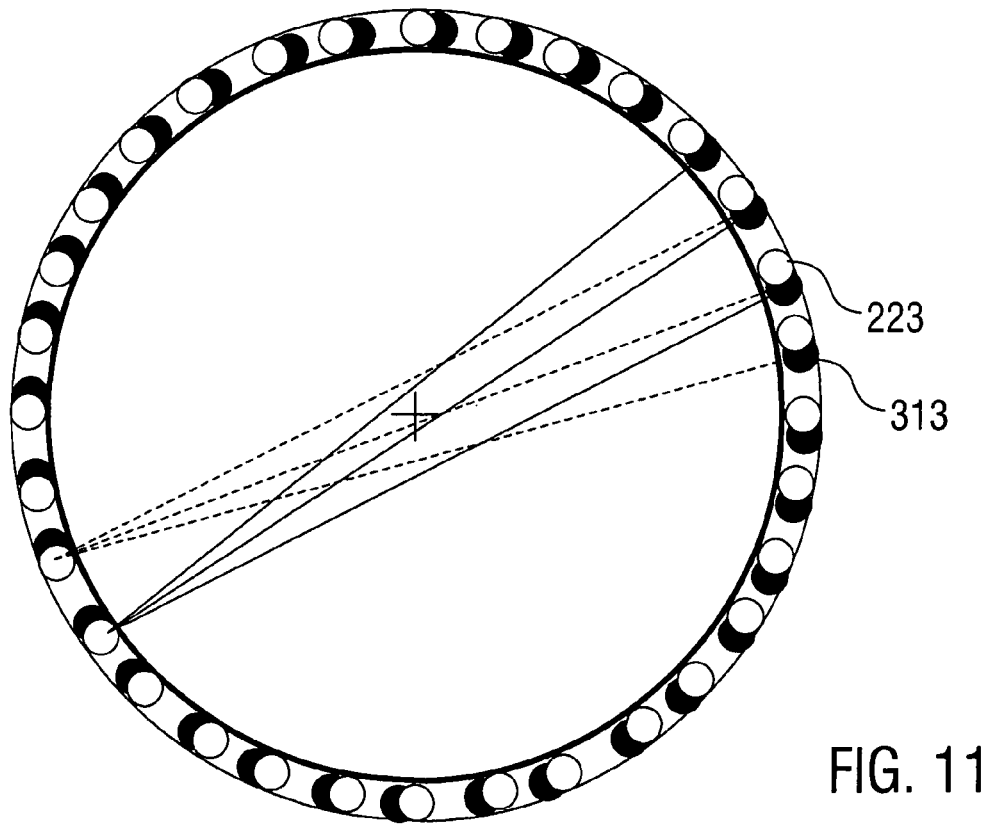
FIGS. 11, 12 further illustrations of Radon data collection used according to the invention.

An essential advantage of the reconstructing method of the invention that influences the design of the imaging device is illustrated in FIG. 11. While the invention has been illustrated in FIGS. 6 to 10 with a rotating combination of a radiation source and the detector device (which could be fixed to each other or moved separately from each other), the invention allows a data collection with a detector device being fixed in the imaging device. Due to the fact that the invention does not need a continuously varying projection direction but only discrete radiation positions of the radiation source, the spacing between the radiation windows 223 (see above) can be used for positioning sensor elements of the detector device. This situation is shown with radiation windows 223 (empty circles) and sensor elements 313 (full circles) arranged adjacent to the radiation windows 223 (FIG. 11).

With a slight tilt between the tube and the detectors this can even be built in a ring within the CT-ring having holes or slices on it. Such a ring would stay unmoved during the investigation and can be used to shut down the radiation in those areas where there is no ray needed according to the geometry. This allows a quite large reduction of X-ray dose in the CT-system due to the fact that the tubes in the systems being used currently are not switched on and off during the turn. A construction like this would not be possible for conventional systems working with filtered back-projection algorithms because quasi continuous data were needed to achieve sufficient reconstruction results. The reduction to single rays would also reduce the problem of scatter radiation, because there are only certain rays from which scatter radiation could occur in the object and these have to be detected by the smaller number of detectors needed.

According to a further embodiment to the invention, the object under investigation can be irradiated with straight, parallel pencil beams emitted simultaneously at each position of the radiation source 210 as shown in FIG. 12. The straight parallel pencil beams 7 are distributed on a radiation field, the extension of which is determined by a elongated radiation source. The parallel pencil beams 7 are shaped with a mask provided on the radiation source as described above. Alternatively, a moving radiation source emitting one pencil beam can be used as it is known from the CT-systems of the first generation. The embodiment of FIG. 12 has the particular advantage that discrete projection profiles can be directly measured with the detector device 310 without the component selection as shown in FIG. 7.

Figure 13:
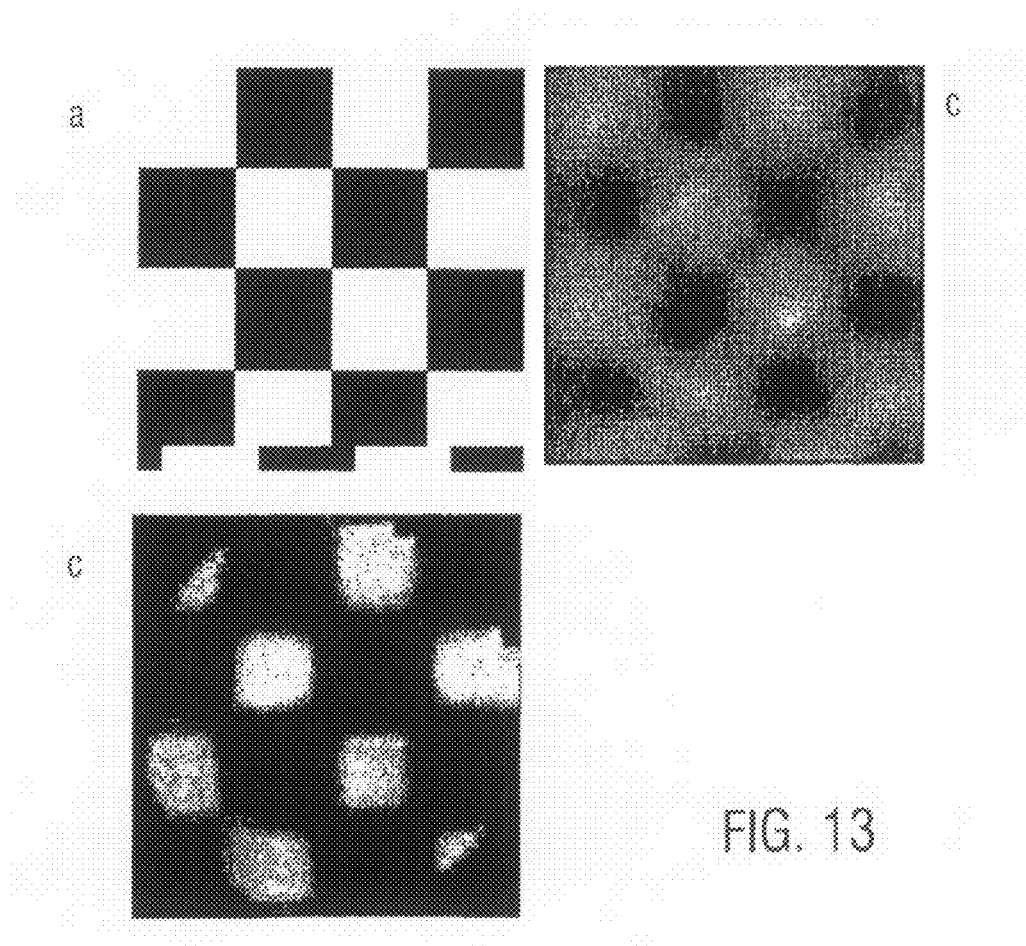
FIG. 13 examples of reconstruction results.

FIG. 13 shows a comparison of an artificial object slice. In part (a) the original object is shown, in part (b) the reconstruction with conventional filtered back-projection using 128 projections, with 32 rays per projection is shown, whereas (c) shows the reconstruction out of 31 projections and 31 rays according to the invention.

Figure 14:
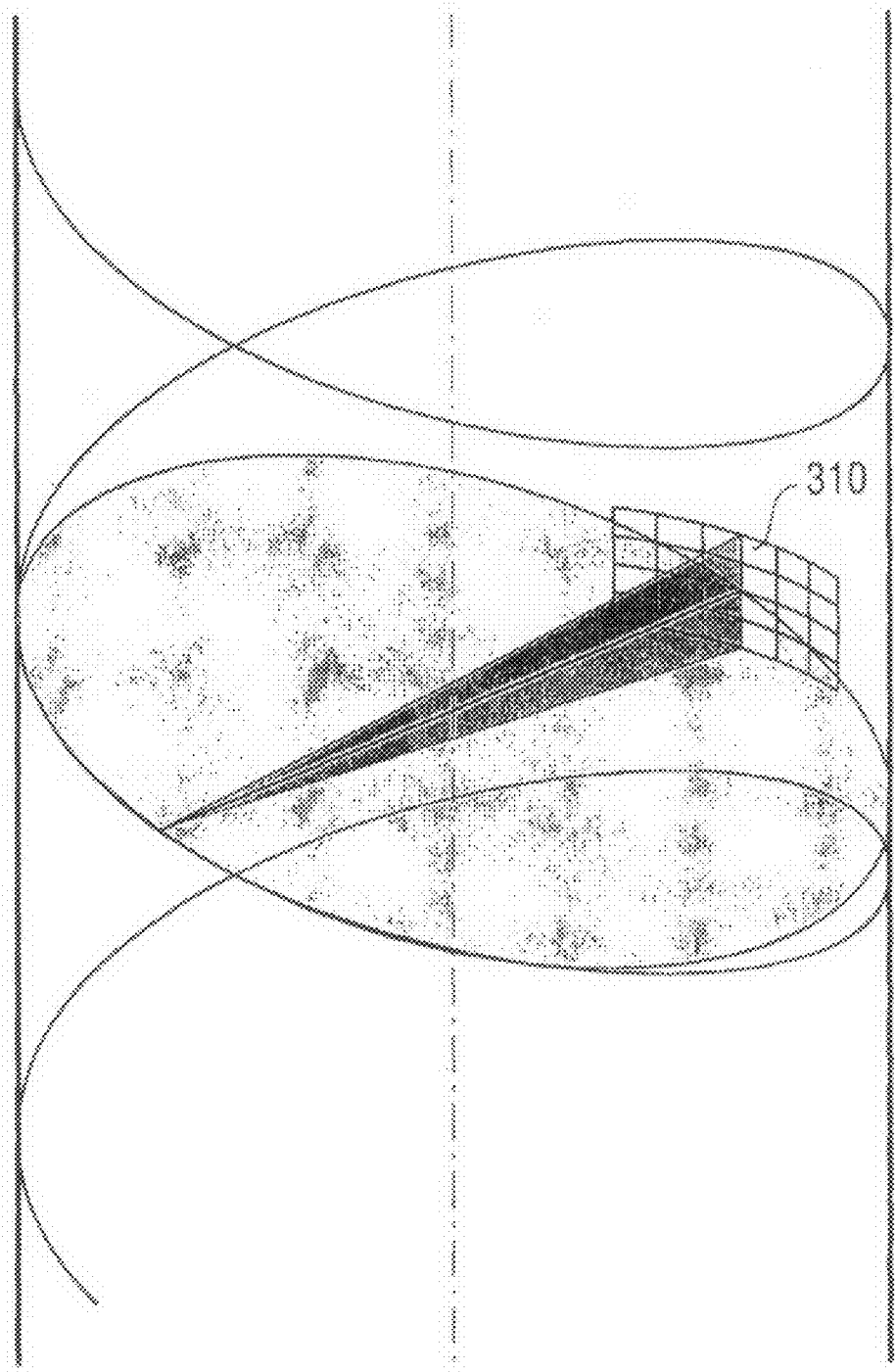
FIG. 14 a schematic illustration of the collection of helical Radon data, and FIGS. 15, 16 schematic illustrations of further embodiments of imaging devices according to the invention.

If the geometry shown in FIG. 2 is extended to 3D imaging, the helical CT currently used in practice can be easily adopted by the invention. FIG. 14 shows the geometric conditions of a helical CT-system and how this can be used with the invention-based reconstruction method. There is a slice through the cylinder that is close to a disc in a plane, which can be reconstructed in the same way as in the 2D case. The steps between the radiation points should be spaced as it is in the 2D case as seen in FIG. 7. In particular, because of the geometry of the CT-scanners with the patient moving along the z-axis, the above mentioned inner ring of holes can still be used (as in FIG. 8).

If one is assuming a multi-slice-CT with detector array 310 instead of a single slice CT, it might be easier to find and select parallel rays through the object for 2D planes.

This is achieved, for example, if a tube with a slice like focal spot (instead of a round spot) is used from which certain rays are chosen by another hole plate along the z-axis or by a ring that has holes or slices on it as mentioned above. In this case one will get data on a cylinder which can be adjusted to single slices. The achievable resolution in the z-axis would again only depend on the number of rays per turn of the machine and on the detector element size.

2.2 Further Imaging Techniques

The above features of imaging an object have been described with reference to X-ray computer tomography. The invention can be applied with other imaging techniques mentioned above in an analogue way.

Figure 15:
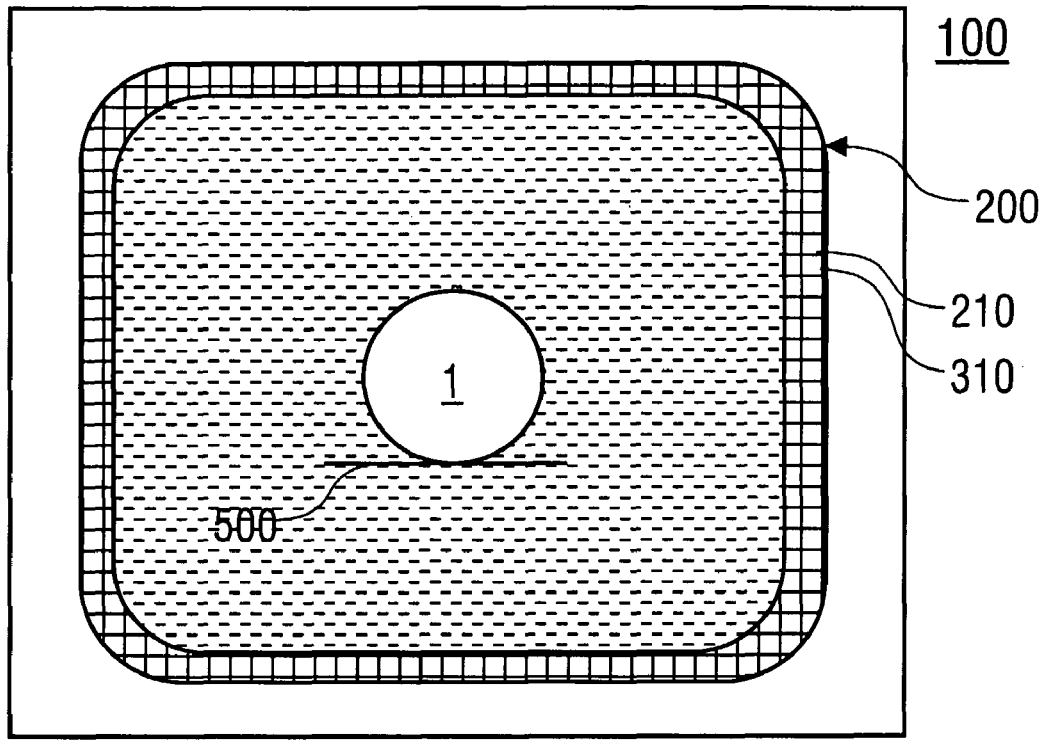

An example for ultrasound tomography of a sample is shown in FIG. 15. The imaging device 100 comprises a fixed arrangement of combined energy generator and detector devices 200, 300 which comprise ultrasound oscillators 210 (converters), ultrasound detectors 310. FIG. 15 illustrates an arrangement with a rectangular arrangement. A corresponding ring-shaped arrangement is possible as well. Within the imaging device 100, an object 1 is arranged on the holding device 500. Advantageously, the effect of the holding device 500 can be introduced into the adjusted matrix with the calibration mentioned above. Between the object 1 and the ultrasound converters, a coupling fluid is arranged. The ultrasound oscillators 210 generate straight ultrasound fields which travel into the object. The ultrasound waves are reflected within the object. The back-reflection is detected with the ultrasound detector 310 and processed according to the principles outlined above.

Figure 16:
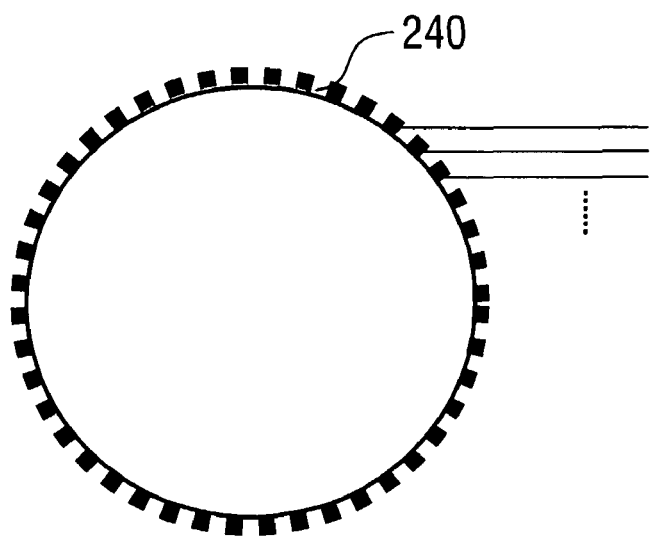

An example for impedance tomography of an object 1 is shown in FIG. 16. The imaging device 100 comprises an arrangement of electrodes 240, being electrically connected with an impedance measurement device. The data being measured as in conventional impedance tomography are used for reconstructing images on the basis of impedance values measured along parallel current directions in the object.

3. Mathematical Description

The method of the invention provides a direct approach for reconstruction of images from Radon data, e.g. in CT. Instead of using the Fourier transform technique as in the filtered back-projection method, the present method is based on orthogonal expansions in terms of orthogonal polynomials of two variables on a disk as outlined in the following. The mathematical background is given in Section (3.1), while the preferred approximations are presented in Section (3.2).

The mathematical description below refers to a disk surrounded by a circle. It is emphasized that an analogue consideration can be done for a region surrounded by an ellipse. With the equation of the ellipse $(x^2/a^2)+(y^2/b^2)=1$, a change of variables $x=au$ and $y=bv$ leads back to the case of the disk $u^2+v^2=1$. Further modified shapes are possible if corresponding changes of variables can be introduced.

For further details of mathematical tools used herein, reference is made to the publications of R. Marr: "On the reconstruction of a function on a circular domain from a sampling of its line integrals" in "J. Math. Anal. Appl." vol. 45, 1974, p. 357-374; F. Natterer: "The mathematics of computerized tomography" Reprint of the 1986 original "Classics in Applied Mathematics 32" SIAM, Philadelphia, Pa., 2001; F. Natterer and F. Wuebbeling by "Mathematical Methods in Image Reconstruction" SIAM, Philadelphia, Pa., 2001; C. Dunkl and Yuan u: "Orthogonal polynomials of several variables", Cambridge University Press, 2001; Yuan Xu "Funk-Hecke formula for orthogonal polynomials on spheres and on balls" in "Bull. London Math. Soc." vol. 32, 2000, p. 447-457; and Yuan Xu "Representation of reproducing kernels and the Lebesgue constants on the ball" in "J. Approximation Theory" vol. 112, 2001, p. 295-310.

3.1 Mathematical Background

Let $B^2=\{(x,y): x^2+y^2\leq 1\}$ denote the unit disk on the plane.

The unit disc is a closed, bounded set with 0 in its interior; is symmetric with respect to 0 (i.e., if q belongs to D, then so does −q); and is convex.

Let θ be an angle measured counterclockwise from the positive x-axis and $l(\theta,t)=\{(x,y): x\cos\theta+y\sin\theta=t\}$ be a line, where $-1\leq t\leq 1$. The notation $$I(\theta,t)=l(\theta,t)\cap B^2, 0\leq\theta<2\pi, -1\leq t\leq 1 \quad (1.1)$$

is used to denote the line segment inside $B^2$. The Radon projection (X-ray) of a function f in the direction (cos θ,sin θ) with parameter $t\in[-1,1]$ is denoted by $R_\theta(f;t)$, $$R_\theta(f;t) := \int_{I(\theta,t)} f(x,y)\,dxdy \quad (1.2)$$

($R_\theta(f;t)$ corresponds to the above function $p_\theta(t)$.)

Let $\Pi_n^2$ denote the space of polynomials of total degree n in two variables, which has dimension $$\dim\Pi_n^2=(n+1)(n+2)/2.$$

Let $V_n(B^2)$ denote the space of orthogonal polynomials of degree n on $B^2$ with respect to the unit weight function; that is, $P\in V_n(B^2)$ if P is of degree n and $$\int_{B^2} P(x,y)Q(x;y)\,dxdy = 0, \text{ for all } Q \in \Pi_{n-1}^2.$$

A set of polynomials $\{P_{j,k}: 0\leq j\leq k\}$ in $V_k(B^2)$ is an orthonormal basis of $V_k(B^2)$ if $$\frac{1}{\pi}\int_{B^2} P_{i,k}(x,y)P_{j,k}(x,y)\,dxdy = \delta_{i,j}, 0\leq i,j\leq k.$$

There are several orthogonal or orthonormal bases that are known explicitly for $V_n(B^2)$ (see C. F. Dunkl and Yuan Xu in "Orthogonal polynomials of several variables", Cambridge Univ. Press, 2001). Here a basis given in terms of ridge polynomials is used.

$U_k$ denotes the Chebyshev polynomial of the second kind, with $$U_k(x) = \frac{\sin(k+1)\theta}{\sin\theta}, x=\cos\theta$$

For $\xi=(\cos\theta, \sin\theta)$ and $X=(x,y)$, the ridge polynomial $U_k(\theta)$ is defined by $$U_k(\theta;x,y):=U_k(\langle X,\xi\rangle)=U_k(x\cos\theta+y\sin\theta).$$

Clearly $U_k$ is an element of $\Pi_k^2$

The zeros of $U_k$ are $\cos\theta_{j,k}, 1\leq j\leq k$, where $\theta_{j,k}=j\pi/(k+1)$.

The following result is illustrated by R. Marr in "On the reconstruction of a function on a circular domain from a sampling of its line integrals" in "J. Math. Anal. Appl." vol. 45, 1974, p. 357-374 (see also Yuan Xu in "FunkHecke formula for orthogonal polynomials on spheres and on balls" in "Bull. London Math. Soc." vol. 32, 2000, p. 447-457).

Lemma 1.1.

An orthonormal basis of $V_n(B^2)$ is given by $$P_k := \{U_k(\theta_{j,k};x,y): 0\leq j\leq k\}, \theta_{j,k}=\frac{j\pi}{k+1}$$

In particular, the set $P_k: \{0\leq k\leq n\}$ is an orthonormal basis for $\Pi_n^2$.

The standard Hilbert space theory shows that any function in $L^2(B^2)$ can be expanded as a Fourier orthogonal series in terms of the orthonormal basis $P_k: \{k\geq 0\}$. More precisely, if $f\in L^2(B^2)$ then $$f = \sum_{k=0}^\infty \sum_{j=0}^k \hat{f}_{j,k} U_k(\theta_{j,k}), \quad (1.3)$$

$$\hat{f}_{j,k} = \frac{1}{\pi}\int_{B^2} f(x,y)U_k(\theta_{j,k};x,y)\,dxdy.$$

The n-th partial sum of the expansion is denoted by $S_n f$; that is, $$S_n f(x,y) = \sum_{k=0}^n \sum_{j=0}^k \hat{f}_{j,k} U_k(\theta_{j,k};x,y),$$

$$\hat{f}_{j,k} = \frac{1}{\pi}\int_{B^2} f(x,y)U_k(\theta_{j,k};x,y)\,dxdy$$

The reconstruction method according to the present invention is based on the following remarkable result, which expresses the partial sum $S_{2m}f$ in terms of the Radon projections.

Theorem 1.2

For $m \geq 0$, the partial sum operator $S_{2m}f$ can be written as $$S_{2m}(f; x, y) = \sum_{v=0}^{2m} \frac{1}{\pi} \int_{-1}^{1} R_{\phi v}(f, t) \Phi_v(t; x, y) dt \quad (1.4)$$

where $$\Phi_v(t; x, y) = \frac{1}{2m+1} \sum_{k=0}^{2m} (k+1) U_k(t) U_k(\phi_v; x, y). \quad (1.5)$$

with $\phi = 2v\pi/(2m+1)$

A similar theorem works for the cylinder region $B_L = B^2 \times [0,L]$, where $L > 0$. Let $v_n^3(B^2)$ be the space of orthogonal polynomials of degree n on $B_L$ with respect to the weight function $$(z(L-z))^{-1/2}/\pi^2;$$

that is, $P \in v_n^3(B_L)$ if $$\frac{1}{\pi^2} \int_{BL} P(x, y, z) Q(x, y, z) dx dy \frac{dz}{\sqrt{z(L-z)}} = 0$$

for all polynomial Q of three variables such that deg Q<n=deg P.

Let $\tilde{T}_k$ be the Chebyshev polynomials of the first kind. Define $\tilde{T}_k$ by $$T_0(z) = 1, \tilde{T}_k(z) = \sqrt{2} T_k(2z/L - 1), k \geq 1$$

The polynomials $\tilde{T}_k$ are orthonormal with respect to $(z(L-z))^{-1/2}/\pi^2$ on $[0, L]$. Let $U_k(\theta_{j,k}; x, y)$ be defined as before.

Lemma 1.3

An orthonormal basis for $v_n^3(B^2)$ is given by $$P_n := \{P_{n,k,j}: 0 \leq j \leq k \leq n\}, P_{n,k,j}(x,y,z) = \tilde{T}_{n-k}(z) U_k(\theta_{j,k}; x, y)$$

In particular, the set $\{P_l: 0 \leq l \leq n\}$ is an orthonormal basis for $\Pi_n^3$.

For $f \in L^2(B_L)$, the Fourier coefficients of $f$ with respect to the orthonormal system $\{P_n: n \geq 0\}$ are given by $$\hat{f}_{n,k,j} = \frac{1}{\pi^2} \int_{BL} f(x, y, z) P_{n,k,j}(x, y, z) dx dy \frac{dz}{\sqrt{z(L-z)}}, 0 \leq j \leq k \leq n$$

Let $S_n f$ denote the Fourier partial sum operator, $$S_n f(x, y, z) = \sum_{l=0}^{n} \sum_{k=0}^{l} \sum_{j=0}^{k} \hat{f}_{l,k,j} P_{j,k,n}(x, y, z)$$

The notation of $R_\phi(g;t)$ for Radon projection of a function $g: B^2 \mapsto R$ is retained. For a fixed z in $[0, L]$, $$R_\phi(f(.,.,z); t) := \int_{l(\phi,t)} f(x; y; z) dx dy \quad (1.6)$$

The following is an analogue of Theorem 1.2 for the cylinder $B_L$.

Theorem 1.4

For $m \geq 0$, $$S_{2m}f(x, y, z) = \frac{1}{2m+1} \quad (1.7)$$

$$\sum_{v=0}^{2m} \frac{1}{\pi^2} \int_{-1}^{1} \int_{0}^{L} R_{\phi v}(f(.,.,w); t) \Phi_v(w; t; x; y; z) \frac{dw \, dt}{\sqrt{w(L-w)}}$$

where $$\Phi_v(w, t; x, y, z) = \sum_{k=0}^{2m} (k+1) U_k(t) U_k(\phi_v; x, y) \sum_{l=0}^{2m-k} \tilde{T}_l(w) \tilde{T}_l(z).$$

In order to make use of the parallel geometry of the Radon data, a quadrature is preferably used according to the invention to get a discrete approximation to the integrals in (1.4) and in (1.7).

If $f$ is a polynomial then $R_\phi(f;.)/\sqrt{1-t^2}$ is also a polynomial. Hence, a quadrature is chosen for the integral with respect to $\sqrt{1-x^2}$ on $[-1,1]$. Such a quadrature is denoted by $I_n g$. Then $$\frac{2}{\pi} \int_{-1}^{1} g(t) \sqrt{1-t^2} dt \approx \sum_{j=1}^{n} \lambda_j g(t_j) := I_n(g), \quad (1.8)$$

where $t_l, \ldots, t_n$ are distinct points in $(-1, 1)$ and $\lambda_j$ are real numbers such that $$\sum_{j=1}^{n} \lambda_j = 1$$

If equality holds in (1.8) for g being polynomials of degree at most ρ, then the quadrature is said to have the degree of exactness ρ.

Among all quadrature formulas, the Gaussian quadrature has the highest degree of exactness. It is given by $$\frac{1}{\pi} \int_{-1}^{1} g(t) \sqrt{1-t^2} dt = \frac{1}{n+1} \sum_{j=1}^{n} g\left(\cos \frac{j\pi}{n+1}\right) := I_n^G(g)$$

for all polynomials g of degree at most 2n−1; that is, its degree of exactness is 2n−1. Note that $j\pi/(n+1)$ are zeros of the Chebyshev polynomial $U_n$.

3.2 Reconstruction Algorithm for the Parallel Geometry
3.2.1 Reconstruction Algorithm for 2D Images Using quadrature formula in (1.4) gives our reconstruction algorithm, which produces a polynomial $A_{2m}f$ defined below.

Algorithm 2.1.

Let $\gamma_{v,j} = R_{\phi v}(f; t_j)..$ (2.1)

For $m \geq 0$ and $(x, y) \in B^2$,, $$A_{2m}(f; x, y) = \sum_{v=0}^{2m} \sum_{j=1}^{n} \gamma_{v,j} T_{j,v}(x, y)$$

where $$T_{j,v}(x, y) = \frac{\lambda_j}{2(2m+1)\sqrt{1-t_j^2}} \Phi_v(t_j; x; y)$$

and $\lambda_j$ and $t_j$ are given in (1.8).

For a given f, the approximation process $A_{2m}f$ uses the Radon data $$\{R_{\phi v}(f;t_j): 0 \leq v \leq 2m, 1 \leq j \leq n\}$$

of $f$. The data consists of Radon projections on 2m+1 equally spaced directions along the circumference of the disk (specified by $\phi_v$) and there are n parallel lines (specified by $t_j$) in each direction. If these parallel Radon projections are taken from an image $f$, then the algorithm produces a polynomial $A_{2m}f$ which gives an approximation to the original image.

The polynomial $A_{2m}f$ is particularly handy for numerical implementation, since one could save $T_{j,v}$, e.g. on a hard disc drive before measurement. This provides a very simple algorithm: given the Radon data, one only has to perform addition and multiplication to evaluate $A_{2m}f(x)$ in (2.1) to get a reconstruction of image.

A good choice of the quadrature is the Gaussian quadrature. If in particular n=2m is chosen, the nodes of the quadrature (1.9) become $t_j=\cos\theta_{j,2m}=\cos j\pi/(2m+1)$. In this case, the algorithm of the invention takes a particular simple form.

Algorithm 2.2.

Let $\gamma_{v,j} = R_{\phi v}(f; \cos\theta_{j,2m})$. (2.2)

For $m \geq 0$, $(x, y) \in B^2$, .

$$A_{2m}(f; x, y) = \sum_{v=0}^{2m} \sum_{j=1}^{2m} \gamma_{v,j} T_{j,v}(x, y)$$

where $$T_{j,v}(x, y) = \frac{1}{(2m+1)^2} \sum_{k=0}^{2m} (k+1)\sin((k+1)\theta_{j,2m})U_k(\phi_v; x, y). \quad (2.3)$$

As a result of the definition, the following consequence is obtained.

Theorem 2.3.

The operator $A_{2m}f$ in Algorithm 2.1 preserves polynomials of degree σ. More precisely, $A_{2m}(f)=f$ whenever $f$ is a polynomial of degree at most σ. In particular, the operator $A_{2m}f$ in Algorithm 2.2 preserves polynomials of degree at most 2m−1.

3.2.2 Reconstruction Algorithm for 2D Images with a Sampling Function (Multiplier Function)

For improving the convergence of the approximation, the method of the invention can start from some summability methods for the Fourier orthogonal expansion that have better convergence behaviour instead of starting from $S_{2m}f$. If the following sampling function (or: multiplier function) is used, advantageously the property that polynomials up to certain degree are preserved is retained. To this end, the sum of polynomials is subjected to a predetermined multiplier function reducing the contributions of polynomials of higher degrees according to the multiplier function.

Definition 2.4.

A function η in $C^r[0,\infty)$, r>0, is called a sampling function if $\eta(t)=1, 0 \leq t \leq 1$, and supp $\pi \subset [0, 2\pi]$.

Let η be a sampling function. An operator $S_{2m}^\eta$ is defined by $$S_{2m}^\eta(f; x, y) = \sum_{k=0}^{2m} \eta\left(\frac{k}{m}\right) \hat{f}_{j,k} U_k(\theta_{j,k}; x, y)$$

It can be proved that the operator $S_{2m}^\eta$ has better approximation property. In fact, if η has third order derivative, then the operator $S_{2m}^\eta$ preserves polynomials of degree up to m and it approximates $f$ as accurate as, up to a constant multiple, any polynomial of degree at most m. The algorithm of the invention is based in this case on the following:

Theorem 2.5.

For $m \geq 0$, the operator $S_{2m}^\eta$ can be written as $$S_{2m}^\eta(f; x, y) = \sum_{v=0}^{2m} \frac{1}{\pi} \int_{-1}^{1} R_{\phi v}(f; t) \Phi_{2m}^\eta(t; x, y) dt \quad (2.4)$$

where $$\Phi_v^\eta(t; x, y) = \frac{1}{2m+1} \sum_{k=0}^{2m} \eta\left(\frac{k}{m}\right)(k+1)U_k(t_j)U_k(\phi_v; x, y). \quad (2.5)$$

Hence, a quadrature can be applied to the integral in (2.4) to get a reconstruction algorithm with a multiplier function. For the Gaussian quadrature (1.9), the following algorithm results.

Algorithm 2.6.

For $m \geq 0$, $(x, y) \in B^2$ (2.6)

$$A_{2m}^\eta(f; x, y) = \sum_{v=0}^{2m} \sum_{j=1}^{2m} R_{\phi v}(f; \cos\theta_{j,2m}) T_{j,v}^\eta(x, y)$$

where $$T_{j,v}^\eta(x, y) = \frac{1}{(2m+1)^2} \sum_{k=0}^{2m} \eta\left(\frac{k}{m}\right)(k+1)\sin((k+1)\theta_{j,2m})U_k(\Phi_v; x, y)$$

For a given f, the approximation process $A_{2m}^\eta f$ uses the same Radon data of $f$ as $A_{2m}f$. It also has the same simple structure for numerical implementation and it preserves polynomials of degree up to m. Its approximation behaviour appears to be better than that of $A_{2m}f$ According to alternative embodiments of the invention, other summability methods, not prescribed by the multiplier function can also be used for improving the convergence.

3.2.3 Reconstruction Algorithm for 3D Images

To obtain an algorithm on the cylinder domain, again the Gaussian quadrature is used. For the integral in z, the Gaussian quadrature for $(z(L-z))^{1/2}$ is used. Set $$\xi_{i,n} = \frac{(2i+1)\pi}{2n} \text{ and } z_i = \frac{1+\cos\xi_{i,n}}{2}, 0 \le i \le n-1$$

where $z_i$ are zeros of $T_n(z)$. The Gaussian quadrature on $[0, L]$ takes the following form, $$\frac{1}{\pi}\int_0^L g(z)\frac{dz}{\sqrt{z(L-z)}} = \frac{1}{n}\sum_{i=0}^{n-1} g(z_1), \quad (2.7)$$

which holds whenever g is a polynomial of degree at most $2n-1$. For the integral in t, the same quadrature (1.8) as in the case of $B^2$ is used. For simplicity, only the reconstruction algorithm using the Gaussian quadrature (1.9) is described. The algorithm produces a polynomial $B_{2m}$ of three variables as follows:

Algorithm 2.7.

Let $\gamma_{v,k,i} = R_{\phi v}(f(.,.,z_i); \cos\psi_{j,2m})$.

For $m \ge 0$, $$B_{2m}f(x; y, z) := \sum_{v=0}^{2m}\sum_{k=1}^{2m}\sum_{i=0}^{n-1} \gamma_{v,k,i} T_{v,k,i}(x, y, z)$$

where $$T_{v,k,i}(x, y, z) = \frac{1}{n(2m+1)}\Phi_v(z_i, \cos\psi_k; x, y, z).$$

For a given function $f$, the approximation process $B_{2m}$ uses the Radon data $$\{R_{\phi v}(f(.,.,z_i; \cos\psi_j): 0 \le v \le 2m, 1 \le j \le 2m, 0 \le i \le n-1)\}$$

of $f$. The data consists of Radon projections on n disks that are perpendicular to the z-axis (specified by $z_i$), on each disk the Radon projections are taken in $2m+1$ equally spaced directions along the circumference of the disk (specified by $\psi_j$) and $2m+1$ parallel lines (specified by $\cos\psi_j$) in each direction. This approximation can be used for the reconstruction of the 3D images from the parallel Radon data. In practice, the integer n of z-direction should be chosen so that the resolution in the z-direction is comparable to the resolution on each disk.

The operator in Algorithm 2.7 preserves polynomials of degree $2m-1$. More precisely, $B_m(f)=f$ whenever $f$ is a polynomial of degree at most $2m-1$.

In the z direction, preferably the weight function $(z(L-z))^{-1/2}$ is used instead of the constant weight function. The reason lies in the fact that the Chebyshev polynomials of the first kind are simple to work with and the corresponding Gaussian quadrature (2.7) is explicit. If the constant weight functions would be used, we would have to work with Legendral polynomials, whose zeros (the nodes of Gaussian quadrature) can be given only numerically.

The reconstruction algorithm for 3D images can be implemented with a sampling function (multiplier function) in an analogue way as outlined above (section 3.2.2).

3.2.4 Convergence of the Algorithm

For the convergence of the above algorithms, it can be shown that the approximation (e.g. Algorithm 2.2) shows a pointwise and uniform convergence if $f$ has second order continuous derivative. In contrast, with the conventional filtered back-projection method, convergence is obtained only for smooth band limited functions (see above F. Natterer).

The invention claimed is:

1. A method of reconstructing an (n+1)-dimensional image function $f$ representing a region of investigation, comprising:
   obtaining an n-dimensional or less dimensional Radon data comprising a plurality of projection functions $p_\Theta(t)$ measured corresponding to a plurality of predetermined projection directions ($\Theta$); and
   with a reconstruction computer, determining the image function $f$ from the n-dimensional or less dimensional Radon data as a sum of polynomials multiplied with values of the projection functions $p_\Theta(t)$.

2. The method of claim 1, wherein the image function $f$ has two, three or four dimensions with n being selected from 1, 2 or 3.

3. The method of claim 1, wherein the polynomials are sums of orthogonal ridge polynomials.

4. The method of claim 1, wherein the projection functions $p_\Theta(t)$ comprise discrete projection profiles, wherein each discrete projection profile comprises projection values $\gamma(vj)$ corresponding to a plurality of projection lines (j) with the same projection direction ($\Theta$).

5. The method of claim 4, wherein integrals in the definition of the polynomials are discretized by a quadrature sum I.

6. The method of claim 5, wherein the integrals in the definition of the polynomials are discretized by the Gaussian quadrature sum I.

7. The method of claim 5, wherein the image function $f$ is determined as a sum of the projection values $\gamma(v,j)$ multiplied by the corresponding elements of a polynomial matrix T.

8. The method of claim 7, further comprising:
   subjecting the polynomial matrix T to a calibration for providing an adjusted polynomial matrix T* in dependence on predetermined conditions of measuring the projection functions.

9. The method of claim 8, wherein the calibration comprises multiplying the polynomial matrix T by a calibration matrix $\beta$ being determined by at least one of an energy distribution function of an energy generator device, a sensitivity distribution function of a detector device and a scattering function of the object.

10. The method of claim 7, wherein at least one of the polynomial matrix T and the adjusted polynomial matrix T* is stored before measuring the projection functions $p_\Theta(t)$.

11. The method of claim 10, wherein the polynomial matrix T, T* is stored in the measuring device before a process of measuring the projection functions.

12. The method of claim 11, wherein the process of measuring the projection functions comprises:
   arranging an object in the measuring device,
   subjecting the object to an energy input directed along the plurality of predetermined projection directions ($\Theta$), and
   measuring the projection functions $p_\Theta(t)$.

13. The method of claim 12, wherein at least one of the object and the measuring device is translated in a predetermined direction during the step of subjecting the object to the energy input for obtaining helical projection data.

14. The method of claim 1, wherein the sum of polynomials is subjected to a predetermined multiplier function reducing the contributions of polynomials of higher degrees according to the multiplier function.

15. The method of claim 1, wherein the image function $f$ is determined from Radon data measured in:
   an X-ray computer tomography (CT) device;
   an ultrasound tomography device;
   a PET imaging device;
   light tomography;
   a Gamma-ray imaging device;
   a SPECT imaging device;
   a neutron based transmission detection system; or
   an electrical impedance tomography device.

16. The method of claim 1, further comprising displaying an image based on the image function $f$.

17. The method of claim 1, further comprising storing the image function $f$.

18. An imaging method for imaging a region of investigation in an object, comprising:
   directing a plurality of energy input beams at predetermined projection directions ($\Theta$) through the region of investigation;
   determining projection functions $p_\Theta(t)$ comprising attenuation values measured with the plurality of energy input beams; and
   subjecting the projection functions $p_\Theta(t)$ to a reconstructing method according to claim 1.

19. The imaging method of claim 18, further comprising:
   representing an approximation of the image function $f$ as a visualized image to be obtained.

20. The imaging method of claim 19, wherein the projection profiles are determined by:
   directing a plurality of pencil beams at predetermined projection directions ($\Theta$) through the region of investigation in the object;
   measuring a plurality of attenuation values for the pencil beams; and
   providing discrete projection profiles, wherein the projection values $\gamma(\nu, j)$ of each discrete projection profile comprise attenuation values corresponding to pencil beams with the same projection direction ($\Theta$), the discrete projection profiles representing the projection functions $p_\Theta(t)$.

21. The imaging method of claim 20, wherein directing a plurality of pencil beams comprises:
   directing a plurality of sets of parallel pencil beams through the region of investigation, wherein each discrete projection profile comprises attenuation values corresponding to one of the sets of parallel pencil beams.

22. The imaging method of claim 20, wherein directing a plurality of pencil beams comprises:
   directing a plurality of sets of discrete fan or cone beams through the region of investigation, wherein each discrete projection profile comprises attenuation values corresponding to fan or cone beam components having the same projection direction ($\Theta$) but being contained in different sets of discrete fan or cone beams.

23. The imaging method of claim 18, wherein the projection functions $p_\Theta(t)$ are determined by:
   directing a plurality of fan or cone beams at predetermined projection directions through the region of investigation; and
   determining the projection functions $p_\Theta(t)$ from the attenuation values measured for each of the fan or cone beams.

24. The imaging method of claim 23, further comprising:
   providing discrete projection profiles, wherein the projection values $\gamma(\nu, j)$ of each discrete projection profile comprise attenuation values corresponding to predetermined fan beam components with the same projection direction ($\Theta$), the discrete projection profiles representing the projection functions $p_\Theta(t)$.

25. The imaging method of claim 18, wherein the projection directions ($\Theta$) are set subsequently by using a movable radiation source being rotated around the object.

26. The imaging method of claim 18, wherein the projection directions ($\Theta$) are set in at least one common plane crossing the region of investigation.

27. The imaging method of claim 18, wherein the projection directions ($\Theta$) are set in varying inclined planes crossing the region of investigation for obtaining helical projection data.

28. The imaging method of claim 18, wherein the object comprises:
   a biological organism or a part thereof,
   a natural phenomenon,
   a fluid composition,
   a solid material,
   a work-piece, and/or
   an object to be investigated for security reasons.

29. An imaging device for imaging a region of investigation in an object, the imaging device comprising:
   a measuring device for measuring projection functions $p_\Theta(t)$ corresponding to a plurality of predetermined projection directions ($\Theta$); and
   a reconstruction circuit for reconstructing an image function $f$ as a sum of polynomials multiplied with values of the measured projection functions $p_\Theta(t)$, the reconstruction circuit being connected with the measuring device.

30. The imaging device of claim 29, wherein the reconstruction circuit is adapted for reconstructing the image function $f$ based on polynomials that are sums of orthogonal ridge polynomials.

31. The imaging device of claim 29, wherein the reconstruction circuit comprises a summation circuit for determining the image function $f$ as a sum of projection values $\gamma_\Theta(\nu, j)$ multiplied by the corresponding elements of a polynomial matrix T, T*.

32. The imaging device of claim 31, wherein the measuring device or the reconstruction circuit comprises a storage for storing the polynomial matrix T, T*.

33. The imaging device of claim 31, wherein the measuring device comprises:
   an energy generator device for directing an energy input through the object; and
   a detector device for measuring the projection functions $p_\Theta(t)$.

34. The imaging device of claim 33, wherein the energy generator device comprises at least one energy input source and a source carrier, wherein the energy input source is movable on the source carrier relative to the object.

35. The imaging device of claim 34, wherein the source carrier has a ring shape and the energy input source is able to be rotated around the object.

36. The imaging device of claim 35, wherein the energy input source is able to be moved along a helical path relative to the object.

37. The imaging device of claim 33, wherein the detector device comprises at least one sensor array for detecting attenuation values representing the attenuation of energy input corresponding to the plurality of predetermined projection directions ($\Theta$).

38. The imaging device of claim 33, wherein the energy input source is a fan or cone beam source for emission of electromagnetic radiation.

39. The imaging device according to claim 38, wherein the fan or cone beam source comprises a source mask for shaping an energy distribution function of the fan or cone beam source, the source mask being movable with the fan or cone beam source.

40. The imaging device of claim 39, wherein the source mask is removable from the energy input source.

41. The imaging device of claim 39, wherein the source mask comprises a plate with through holes, the plate being made of an energy input shielding material.

42. The imaging device of claim 33, wherein the energy input source is a pencil beam source for emission of electromagnetic or particle radiation.

43. The imaging device of claim 42, wherein the pencil beam source comprises a source mask for arranging a plurality of pencil beams, the source mask being movable with the pencil beam source.

44. The imaging device of claim 43, wherein the source mask is removable from the energy input source.

45. The imaging device of claim 43, wherein the source mask comprises a plate with through holes, the plate being made of an energy input shielding material.

46. The imaging device of claim 33, wherein the energy generator device comprises a plurality of frame masks for shaping an energy distribution function of the energy input source, the frame masks being fixed on the source carrier at predetermined positions.

47. The imaging device of claim 46, wherein the positions of the frame masks are spaced by equal arc lengths.

48. The imaging device of claim 46, wherein the source carrier comprises a ring-shaped shield containing the frame masks, the ring-shaped shield shielding the energy input source at positions other than the positions of the frame masks.

49. The imaging device of claim 33, wherein the detector device comprises a plurality of frame sensors for detecting attenuation values representing the attenuation of energy input corresponding to the plurality of predetermined projection directions ($\Theta$), the frame sensors being fixed on the source carrier at predetermined positions.

50. The imaging device of claim 49, wherein the frame sensors are positioned adjacent to the frame masks.

51. The imaging device of claim 33, wherein the measuring device comprises:
   an X-ray computer tomography (CT) device;
   an ultrasound tomography device;
   a PET imaging device;
   light tomography device;
   a Gamma-ray imaging device;
   a SPECT imaging device;
   a neutron based transmission detection system; or
   an electrical impedance tomography device.

52. A computer readable medium comprising computer-executable instructions for reconstructing an (n+1)-dimensional image function $f$ representing a region of investigation by:
   obtaining an n-dimensional or less dimensional Radon data comprising a plurality of projection functions $p_\Theta(t)$ measured corresponding to a plurality of predetermined projection directions ($\Theta$); and
   determining the image function $f$ from the n-dimensional or less dimensional Radon data as a sum of polynomials multiplied with values of the projection functions $p_\Theta(t)$.

53. Computer-readable medium comprising computer-executable instructions for digital storage media or computer program product with electronically readable data comprising a polynomial matrix T, said data being able to interact with a calculation unit in the imaging device according to claim 33 for conducting a method of reconstructing an (n+1)-dimensional image function $f$ representing a region of investigation, comprising:
   obtaining an n-dimensional or less dimensional Radon data comprising a plurality of projection functions $p_\Theta(t)$ measured corresponding to a plurality of predetermined projection directions ($\Theta$); and
   determining the image function $f$ from the n-dimensional or less dimensional Radon data as a sum of polynomials multiplied with values of the projection functions $p_\Theta(t)$.

* * * * *

UNITED STATES PATENT AND TRADEMARK OFFICE
CERTIFICATE OF CORRECTION

PATENT NO. : 8,081,807 B2
APPLICATION NO. : 11/794558
DATED : December 20, 2011
INVENTOR(S) : Xu et al.

Page 1 of 1

It is certified that error appears in the above-identified patent and that said Letters Patent is hereby corrected as shown below:

In the Specification:

Column/Lines: 1/20-24

Error: This invention was made with Government support under Grant No. DMS-02011669 awarded by the National Science Foundation, U.S.A. The Government of the United States of America has certain rights in the invention.

Correction: This invention was made with Government support under Grant No. DMS-0201669 awarded by the National Science Foundation, U.S.A. The Government of the United States of America has certain rights in the invention.

Column 19, line 28, "u:" should read --Xu:--.

Column 21, line 35, " $\sqrt{2T_k}$ " should read -- $\sqrt{2T_k}$ --.

Column 25, lines 56-57, "$(z(L-z))^{-1/2}$" should read --$(z(L-z))^{-1/2}$--.

In the Claims:

Column 26, line 26, "γ(vj)" should read --γ(v,j) --.

Signed and Sealed this
Sixteenth Day of June, 2015

Michelle K. Lee
*Director of the United States Patent and Trademark Office*